US008545835B2

(12) United States Patent
Dalgleish et al.

(10) Patent No.: US 8,545,835 B2
(45) Date of Patent: *Oct. 1, 2013

(54) HUMAN PROSTATE CELL LINES IN CANCER TREATMENT

(75) Inventors: Angus George Dalgleish, London (GB); Anthony Ian Walker, London (GB)

(73) Assignee: Onyvax Limited (GB)

( * ) Notice: Subject to any disclaimer, the term of this patent is extended or adjusted under 35 U.S.C. 154(b) by 0 days.

This patent is subject to a terminal disclaimer.

(21) Appl. No.: 13/351,349

(22) Filed: Jan. 17, 2012

(65) Prior Publication Data

US 2013/0017222 A1    Jan. 17, 2013

Related U.S. Application Data

(63) Continuation of application No. 12/206,174, filed on Sep. 8, 2008, now Pat. No. 8,097,244, which is a continuation of application No. 10/897,426, filed on Jul. 23, 2004, now Pat. No. 7,438,922, which is a continuation-in-part of application No. 10/624,889, filed on Jul. 23, 2003, now abandoned.

(51) Int. Cl.
    *A61K 35/48*    (2006.01)

(52) U.S. Cl.
    USPC ....... 424/93.3; 424/93.7; 424/277.1; 424/573

(58) Field of Classification Search
    None
    See application file for complete search history.

(56) References Cited

U.S. PATENT DOCUMENTS

| 5,804,443 | A | 9/1998 | Bernofsky |
| 6,699,483 | B1 | 3/2004 | Dalgleish et al. |
| 6,972,128 | B1 | 12/2005 | Dalgleish et al. |
| 7,438,922 | B2 | 10/2008 | Dalgleish et al. |
| 8,097,244 | B2 | 1/2012 | Dalgleish et al. |
| 2003/0185808 | A1 | 10/2003 | Thraves et al. |
| 2005/0019336 | A1 | 1/2005 | Dalgleish et al. |
| 2005/0058668 | A1 | 3/2005 | Dalgleish et al. |

FOREIGN PATENT DOCUMENTS

| WO | WO 93/06867 | 4/1993 |
| WO | WO 95/29704 | 11/1995 |
| WO | WO 97/18296 | 5/1997 |
| WO | WO 97/24132 | 7/1997 |
| WO | WO 97/28255 | 8/1997 |
| WO | WO 98/16238 | 4/1998 |
| WO | WO 99/19462 | 4/1999 |
| WO | WO 00/04918 | 2/2000 |
| WO | WO 00/33869 | 6/2000 |
| WO | WO 00/33870 | 6/2000 |
| WO | WO 00/71155 | 11/2000 |
| WO | WO 01/75073 | 10/2001 |

OTHER PUBLICATIONS

Ablin, J. Cancer Res. Clin. Oncol. 123: 583-594 (1997).
Bellone et al., Immunology Today 20(10): 456-461 (1999).
Berthon, Intl J Oncology, 6(2): 333-343 (1995).
Boon, Adv Can Res 58: 177-210 (1992).
Brenner et al., Journal of Urology, pp. 1575-1579 (1995) (abstract only).
Bright et al., Cancer Research (57)(1): 995-1002 (1997).
Carducci et al., Journal of Clinical Oncology 21(4): 679-689 (2003).
Clark, Protein Engineering of Antibody Molecules for Prophylactic and Therapeutic Applications in Man, p. 1 (1993).
Corbel, Dev. Biol. Stand. 87: 113-124 (1996) (abstract only).
Curti, Crit. Rev, in Oncology/Hematology 14:29-39 (1993).
D'Amico et al., American Society of Clinical Oncology, Abstract No. 4506 (2004).
Dermer, Bio/Technology 12:320 (1994).
Diederichsen et al., Oncology Reports 5: 823-826 (1998).
Dillman et al., Cancer Biotherapy & Radiopharmaceuticals 15(2): 161-168 (2000).
Drexler et al., Leukemia and Lymphoma 9:1-25 (1993).
Eaton et al., BJU International 89: 19-26 (2002).
Embleton et al., Immunol Ser 23:181-207 (1984).
Engel et al., Scand. J. Immunol. 45: 463-470 (1997).
Esparaza et al., J. of Immnology 131(5): 2117-2121 (1983).
Fenton et al., J. of Immunotherapy 19(5): 364-374 1996).
Fogel et al., J. Natl. Cancer Inst. 62(3):585-588 (1979).
Freshney, Culture of Animal Cells, a Manual of Basic Technique, Alan R. Liss, Inc., New York, p. 4 (1983).
Gorelik et al., Journal of Supramolecular Structure 12: 385-402 (1979) (abstract only).
Gura, Science 278:1041-1042 (1997).
Hartwell et al., Science 278:1064-1068 (1997).
Hrouda et al., BJU International 86: 742-748 (2000).
Hsu, Tissue Culture Methods and Applications, Kruse and Patterson, Eds., Academic Press, NY, pp. 764767 (1973).
Jäger et al. Int. J. Cancer 71: 142-147 (1997).
Jain, Sci. Am. 271:58-65 (1994).
Kayaga et al., Gene Therapy 6: 1475-1481 (1999).
Kusumoto et al., Cancer Immunol Immunother 50: 373-381 (2001).
Kylstra et al., Proceedings of the AACR, vol. 44, $2^{nd}$ ed., Abstract No. 5396 (2003).
Lehner et al., Cancer Immunol Immunother 32: 173-178 (1990).
Maitland et al., Radiation Research 155: 133-142 (2001).
Marble, Cancer Weekly Plus, p. 4(2) (1997).
Moran, American Medical News 42, 39, 23 (1999).
Nelson et al., American Society of Clinical Oncology, Abstract No. 4554 (2004).
Olumi et al., Cancer Research 58: 4525-4530 (1998).
Schreiber et al., Human Gene Therapy 10: 983-993 (1999).
Small et al., Journal of Clinical Oncology 18(23): 3894-3903 (2000).
Tamura et al., Science 278: 117-120 (1997).
Tjoa et al., The Prostate 27: 63-69 (1995).
Triest et al., Clinical Cancer Res. 4(8): 2009-14 (1998).
Usmani et al., Clinical Science 103(48): 314S-317S (2002).
Vermorken et al., The Lancet 353: 345-350 (1999). Vieweg et al., Cancer Research 54: 1760-1765 (1994).
Volpe, Cancer Genet Cytogenet 34: 125-134 (1988).
Weiner, Seminars Oncology 26(4)(12): 41-50 (1999).
Wu et al., Intl J cancer, 77(6): 887-94 (1998).
Zhau et al., Proc. Natl. Acad. Sci. USA 93: 15152-15157 (1996).
ATCC catalog entry for LnCap (downloaded from the Web on Jun. 16, 2010.
ATCC catalog entry for DU145 (downloaded from the Web on Jun. 16, 2010.
ATCC catalog entry for PC3 (downloaded from the Web on Jun. 16, 2010.

*Primary Examiner* — Karen Canella
(74) *Attorney, Agent, or Firm* — Perkins Coie LLP

(57) ABSTRACT

The invention provides methods and compositions for the treatment of primary, metastatic, and residual cancer in mammals, and more particularly, the use of materials such as whole cells and derivatives and portions thereof to stimulate the immune system to attack cancer.

13 Claims, 26 Drawing Sheets

1 = Molecular weight markers, 2 = PNT2 lysate, 3 = 1542 lysate, 4 = DU145 lysate, 5 = LnCap lysate 1 = Molecular weight markers, 2 = PNT2 lysate, 3 = 1542 lysate, 4 = DU145 lysate, 5 = LnCap lysate Patient 304 Pre Vaccination 1 = Molecular weight markers, 2 = PNT2 lysate, 3 = 1542 lysate, 4 = DU145 lysate, 5 = LnCap lysate 1 = Molecular weight markers, 2 = PNT2 lysate, 3 = 1542 lysate, 4 = DU145 lysate, 5 = LnCap lysate Patient 402 Pre Vaccination 1 = Molecular weight markers, 2 = PNT2 lysate, 3 = 1542 lysate, 4 = DU145 lysate, 5 = LnCap lysate Patient 402 Post Vaccination 1 = Molecular weight markers, 2 = PNT2 lysate, 3 = 1542 lysate, 4 = DU145 lysate, 5 = LnCap lysate

| Patient | Slope Pre treatment | Slope Post treatment | Doubling time (days) Pre-treatment | Doubling time (days) Post treatment | |
|---|---|---|---|---|---|
| 1 | 0.0038 | 0.0014 | 182 | 495 | p = 0.04 |
| 2 | 0.0065 | 0.0068 | 106 | 102 | |
| 3 | 0.0046 | 0.0033 | 152 | 213 | |
| 4 | 0.0041 | 0.0032 | 169 | 217 | |
| 5 | 0.0043 | 0.0018 | 161 | 377 | p = 0.08 |
| 6 | 0.0021 | 0.0235 | 324 | 29 | |
| 7 | 0.0038 | 0.0015 | 184 | 475 | p = 0.1 |
| 8 | 0.0046 | 0.0053 | 150 | 130 | |
| 9 | 0.009 | 0.0041 | 77 | 168 | p = 0.005 |
| 10 | 0.0113 | 0.0064 | 61 | 109 | p = 0.009 |
| 11 | 0.003 | 0.0027 | 234 | 261 | |
| 12 | 0.0072 | 0.0028 | 96 | 248 | p = 0.001 |
| 13 | 0.0075 | 0.0123 | 92 | 56 | |
| 14 | 0.0157 | 0.0024 | 44 | 294 | p = 0.004 |
| 15 | 0.00002 | 0.0033 | 2999 | 213 | |

FIG. 9

HUMAN PROSTATE CELL LINES IN CANCER TREATMENT

This application is a continuation of U.S. application Ser. No. 12/206,174 filed Sep. 8, 2008, now U.S. Pat. No. 8,097,244, which is a continuation of U.S. application Ser. No. 10/897,426 filed Jul. 23, 2004, now U.S. Pat. No. 7,438,922, which is a continuation-in-part of U.S. application Ser. No. 10/624,889, filed Jul. 23, 2003, the entireties of which are hereby incorporated by reference.

FIELD OF THE INVENTION

Combinations of cell lines are provided for allogeneic immunotherapy agents in the treatment of cancer. Cancer vaccines generally have been limited to the use of cells that contain at least some tumour specific antigens ("TSAs") and/or tumour associated antigens ("TAAs") having shared identity with antigens in a targeted tumour. In such cases, tumour cells often are utilised as a starting point on the premise that only tumour cells will contain TSAs or TAAs or relevance, and the tissue origins of the cells are matched to the tumour site in patients. A primary aspect of the invention is the use of immortalised normal, non-malignant cells, in combination with primary and/or metastatic tumour cells, as the basis of an allogeneic cell cancer vaccine. Normal cells do not posses TSAs or relevant concentrations of TAAs and hence it is surprising that normal cells are effective as anti-cancer vaccines when administered in combination with primary and/or metastatic tumour cells. More surprisingly, a three way combination of cells obtained from metastasised cells, non metastasised tumour and cells from a normal cell line provided good therapy. For prostate cancer, for example, a vaccine may be based on one or a combination of different immortalised normal cell lines derived from the prostate according to parameters described herein. The cell lines may be lethally irradiated with, for example, gamma irradiation at 50-300 Gy to ensure that they are replication incompetent prior to use.

BACKGROUND TO THE INVENTION

Cancerous cells contain numerous mutations that can result in recognition of the cells by a host's immune system. Appreciation of this phenomenon has prompted much research into potential immunotherapies to harness the host's immune system for attacking cancer cells. Eliminating these cells or reducing them to a level that is not life-threatening has been a major goal, as reviewed in Maraveyas, A. & Dalgleish, A. G. 1997 *Active immunotherapy for solid tumours in vaccine design* in The Role of Cytokine Networks, Ed. Gregoriadis et al., Plenum Press, New York, pages 129-145; Morton, D. L. and Ravindranath, M. H. 1996 *Current concepts concerning melanoma vaccines* in Tumor Immunology—Immunotherapy and Cancer Vaccines, ed. Dalgleish, A. G. and Browning, M., Cambridge University Press, pages 241-268.

Such work in the cancer immunotherapy field can be classified into five categories, non-specific immunotherapy, antibodies and monoclonal antibodies, subunit vaccines, gene therapy, and cell-based vaccines.

Non-Specific Immunotherapy

Efforts to stimulate the immune system non-specifically date back over a century to the pioneering work of William Coley (Coley, W. B., 1894 Treatment of inoperable malignant tumours with toxins of erisipelas and the *Bacillus prodigosus*. Trans. Am. Surg. Assoc. 12: 183). Although successful in a limited number of cases (e.g. BCG (i.e. bacille Calmette-Guérin) for the treatment of urinary bladder cancer, IL-2 for the treatment of melanoma and renal cancer) it is widely acknowledged that non-specific immunomodulation is unlikely to prove sufficient to treat the majority of cancers. While non-specific immune-stimulants may lead to a general enhanced state of immune responsiveness, they lack the targeting capability and also subtlety to deal with tumour lesions which have many mechanisms and plasticity to evade, resist and subvert immune-surveillance.

Antibodies and Monoclonal Antibodies

Passive immunotherapy in the form of antibodies, and particularly monoclonal antibodies, has been the subject of considerable research and development as anti-cancer agents. Originally hailed as the magic bullet because of their exquisite specificity, monoclonal antibodies have failed to live up to their expectation in the field of cancer immunotherapy for a number of reasons, including immune responses to the antibodies themselves and inability of the antibody to access the lesion through the blood vessels (thereby abrogating their activity). To date, few products have been registered as pharmaceuticals for human use, notably Rituxan (IDEC/Genentech/Hoffman la Roche) and Herceptin (Genentech/Hoffman la Roche) with over 50 other projects in the research and development pipeline. Antibodies also may be employed in active immunotherapy utilizing anti-idiotype antibodies which appear to mimic (in an immunological sense) cancer antigens. Although elegant in concept, the utility of antibody-based approaches may ultimately prove limited by the phenomenon of 'immunological escape,' where a subset of cancer cells in a mammalian or human subject mutates and loses the antigen recognized by the particular antibody and thereby can lead to the outgrowth of a population of cancer cells that are no longer treatable with that antibody.

Subunit Vaccines

Drawing on the experience in vaccines for infectious diseases and other fields, many researchers have sought to identify antigens that are exclusively or preferentially associated with cancer cells, namely tumour specific antigens (TSA) or tumour associated antigens (TAA), and to use such antigens or fractions thereof as the basis for specific active immunotherapy.

There are numerous ways to identify proteins or peptides derived therefrom which fall into the category of TAA or TSA. For example, it is possible to utilize differential display techniques whereby RNA expression is compared between tumour tissue and adjacent normal tissue to identify RNAs which are exclusively or preferentially expressed in the lesion. Sequencing of the RNA has identified several TAA and TSA which are expressed in that specific tissue at that specific time, but therein lies the potential deficiency of the approach in that identification of the TAA or TSA represents only a "snapshot" of the lesion at any given time which may not provide an adequate reflection of the antigenic profile in the lesion over time. Similarly a combination of cytotoxic T lymphocyte (CTL) cloning and expression-cloning of cDNA from tumour tissue has lead to identification of many TAA and TSA, particularly in melanoma. The approach suffers from the same inherent weakness as differential display techniques in that identification of only one TAA or TSA may not provide an appropriate representation of a clinically relevant antigenic profile.

Over fifty subunit vaccine approaches are in development for treating a wide range of cancers, although none has yet received marketing authorization for use as a human pharmaceutical product. In a similar manner to that described for antibody-based approaches above, subunit vaccines also may be limited by the phenomenon of immunological escape.

Gene Therapy

Most gene therapy trials in humans concern cancer treatment. A substantial proportion of these trial have purported to trigger and/or amplify patients' immune responses. Of particular note in are Allovectin-7 and Leuvectin, developed by Vical Inc for a range of human tumours, and StressGen Inc.'s stress protein gene therapy for melanoma and lung cancer. It is too early to judge whether these and the other 'immunogene therapies' in development by commercial and academic bodies ultimately will prove successful. However the commercial utility of these approaches are expected to be more than a decade away.

Cell-Based Vaccines

Tumours have the remarkable ability to counteract the immune system in a variety of ways. These include, down-regulating the expression of potential target proteins; mutation of potential target proteins; downregulating surface expression of receptors and other proteins; downregulating MHC class I and II expression thereby hindering direct presentation of TAA or TSA peptides; downregulating co-stimulatory molecules leading to incomplete stimulation of T-cells and thus to anergy; shedding of selective, non representative membrane portions that act as decoys to the immune system; shedding of selective membrane portions that anergise the immune system; secreting inhibitory molecules; inducting T-cell death; and other ways. Because of this wide diversity of escape mechanisms, their immunological heterogeneity and plasticity, tumours growth has to be matched with suitable immunotherapeutic strategies that can account for such heterogeneity. The potential advantages are:

(a) whole cells contain a broad range of antigens, providing an antigenic profile of sufficient heterogeneity to match that of the lesions as described above;
(b) being multivalent (i.e. containing multiple antigens), the risk of immunological escape is reduced (the probability of cancer cells 'losing' all of these antigens is remote); and
(c) cell-based vaccines include TSAs and TAAs that have yet to be identified as such; it is possible if not likely that currently unidentified antigens may be clinically more relevant than the relatively small number of TSAs/TAAs that are known.

Cell-based vaccines fall into two categories. The first category uses autologous cells. Typically a procedure within this category begins with taking a biopsy from a patient, cultivating tumour cells from the biopsy in vitro, modifying the cultivated cells through transfection and/or other means, irradiating the modified cells to render them replication-incompetent, and then injecting the replication-incompetent cells back into the same patient as a vaccine. Although this approach enjoyed considerable attention over the past decade, it has been increasingly apparent that this individually-tailored therapy is inherently impractical for several reasons. The procedure is time consuming as the lead time for producing clinical doses of vaccine often may exceed the patients' life expectancy. The procedure may be expensive and, as a 'bespoke' product, it is not possible to specify a standardised product (only the procedure, not the product, can be standardised and hence optimised and quality controlled). Still further, the tumour biopsy used to prepare the autologous vaccine generally will have unique growth characteristics, interactions and communications with surrounding tissue. The characteristics of the initial cell sample, which reflect a particular environment at a single time point from a tumour may severely limit the use of autologous cells for immunotherapy:, wherein a vaccine desirably may be administered over the entire presentation time of a disease.

The second category of cell-based vaccines utilize allogeneic cells. These vaccines comprise cells that that genetically (and hence immunologically) are mismatched to patients. Allogeneic cell procedures benefit from the same advantages of multivalency as autologous cells. In addition, allogeneic cell vaccines can utilize immortalized cell lines, which can be cultivated indefinitely in vitro. Thus, this approach overcomes the lead-time and cost disadvantages of autologous methodologies.

Numerous publications extol the utility of cell-based cancer vaccines. See, for example, Dranoff, G. et al. WO 93/06867; Gansbacher, P. WO 94/18995; Jaffee, E. M. et al. WO 97/24132; Mitchell, M. S. WO 90/03183; and Morton, D. M. et al. WO 91/06866. These studies report procedural variations that range from a basic technique of using cancer cells as an immunotherapy antigen, to transfecting the cells to produce GM-CSF, IL-2, interferons or other immunologically-active molecules to the use of 'suicide' genes. Various research groups have reported the use of allogeneic cell lines for use against melanoma, that are HLA-matched or partially-matched to a patients' haplotype and allogeneic cell lines that are mismatched to the patients' haplotype. Also described are mismatched allogeneic prostate cell lines transfected with GM-CSF.

Despite this intensive work in a crucial field of medical science, successful and reproducible eradication or inhibition of cancer growth remains elusive. Any new material or procedure that can address and at least partially overcome the limitations inherent in the use of cell based vaccines would provide very important benefits for treatment of this disease. These needs are satisfied by the present invention.

SUMMARY OF THE INVENTION

Embodiments of the invention alleviate the problems in the field summarized above in several ways. One embodiment provides an allogeneic immunotherapy vaccine for the treatment of prostate cancer in a patient, comprising an adjuvant, cells from a first allogeneic normal prostate cell line, cells from a second allogeneic cell line obtained from a primary prostate cancer biopsy, and cells from a third allogeneic cell line obtained from a metastasis of prostate cancer.

Another embodiment provides an allogeneic immunotherapy vaccine for the treatment of prostate cancer in a patient, comprising an adjuvant, allogeneic cells from a first normal prostate cell line, allogeneic cells from a second immortalized cell line obtained from a prostate cancer biopsy, and allogeneic cells from a third immortalized line obtained from a prostate cancer biopsy, wherein cells of the second immortalized cell line express normal levels of neutral endopeptidase but low levels of endothelin converting enzyme and cells of the third immortalized cell line express low levels of both neutral endopeptidase and endothelin converting enzyme.

Yet another embodiment provides an allogeneic immunotherapy vaccine for the treatment of prostate cancer in a patient, comprising an adjuvant and a combined vaccine ONY-P1, wherein the ONY-P1 comprises allogeneic cells from a first normal prostate cell line, allogeneic cells from a second immortalized cell line obtained from a prostate cancer metastasis biopsy, and allogeneic cells from a third immortalized line obtained from a prostate cancer metastasis biopsy.

One aspect of the invention provides methods of inhibiting progression of prostate cancer in a patient, comprising administering the patient an effective amount of an allogeneic immunotherapy vaccine, wherein the vaccine comprises an adjuvant and a combined vaccine ONY-P1, wherein the ONY- P1 comprises allogeneic cells from a first normal prostate cell line, allogeneic cells from a second immortalized cell line obtained from a prostate cancer biopsy, and allogeneic cells from a third immortalized line obtained from a prostate cancer biopsy. In another aspect, the invention provides methods of increasing PSA doubling times (PSADT) in a prostate cancer patient by administering the patient an effective amount of the allogeneic immunotherapy vaccine.

Another aspect of the invention provides methods of inhibiting progression of prostate cancer in a patient, comprising administering the patient an effective amount of an allogeneic immunotherapy vaccine, wherein the vaccine comprises an adjuvant, cells from a first allogeneic normal prostate cell line, cells from a second allogeneic cell line obtained from a primary prostate cancer biopsy, and cells from a third allogeneic cell line obtained from a metastasis of prostate cancer. In another aspect, the invention provides methods of increasing PSADT in a prostate cancer patient by administering the patient an effective amount of the allogeneic immunotherapy vaccine.

Another aspect of the invention provides methods of inhibiting progression of prostate cancer in a patient, comprising administering the patient an effective amount of an allogeneic immunotherapy vaccine, wherein the vaccine comprises an adjuvant, cells from a first allogeneic normal prostate cell line, cells from a second allogeneic cell line obtained from a primary prostate cancer biopsy, and cells from a third allogeneic cell line obtained from a metastasis of prostate cancer, wherein the cells of the second allogeneic cell line exhibit tumour associated glycoprotein related to sialyated Tn antigen. In another aspect, the invention provides methods of increasing PSADT in a prostate cancer patient by administering the patient an effective amount of the allogeneic immunotherapy vaccine.

In another aspect, the invention provides methods of inhibiting progression of prostate cancer in a patient, comprising administering the patient an effective amount of an allogeneic immunotherapy vaccine, wherein the vaccine comprises an adjuvant, allogeneic cells from a first normal prostate cell line, allogeneic cells from a second immortalized cell line obtained from a prostate cancer biopsy, and allogeneic cells from a third immortalized line obtained from a prostate cancer biopsy. In another aspect, the invention provides methods of increasing PSADT in a prostate cancer patient by administering the patient an effective amount of the allogeneic immunotherapy vaccine.

Yet in another aspect, the invention provides methods of inhibiting progression of prostate cancer that has metastasised to a tissue selected from the group consisting of bone, lymph node, brain and liver in a patient, comprising administering the patient an effective amount of an allogeneic immunotherapy vaccine, wherein the vaccine comprises an adjuvant, allogeneic cells from a first normal prostate cell line, allogeneic cells from a second immortalized cell line obtained from a prostate cancer biopsy, and allogeneic cells from a third immortalized line obtained from a prostate cancer that has metastasised. Yet in another aspect, the invention provides methods of increasing PSADT in a prostate cancer patient by administering the patient an effective amount of the allogeneic immunotherapy vaccine.

Other embodiments will be appreciated by a skilled artisan upon reading the specification. Many of these embodiments concern selected cell lines used in allogeneic immunotherapy agents for the treatment of cancer. These types of vaccine provided unexpected favourable clinical outcomes.

BRIEF DESCRIPTION OF THE DRAWINGS

FIG. 9 shows PSA doubling time results for 15 patients.

DETAILED DESCRIPTION OF THE INVENTION

Figure 1:
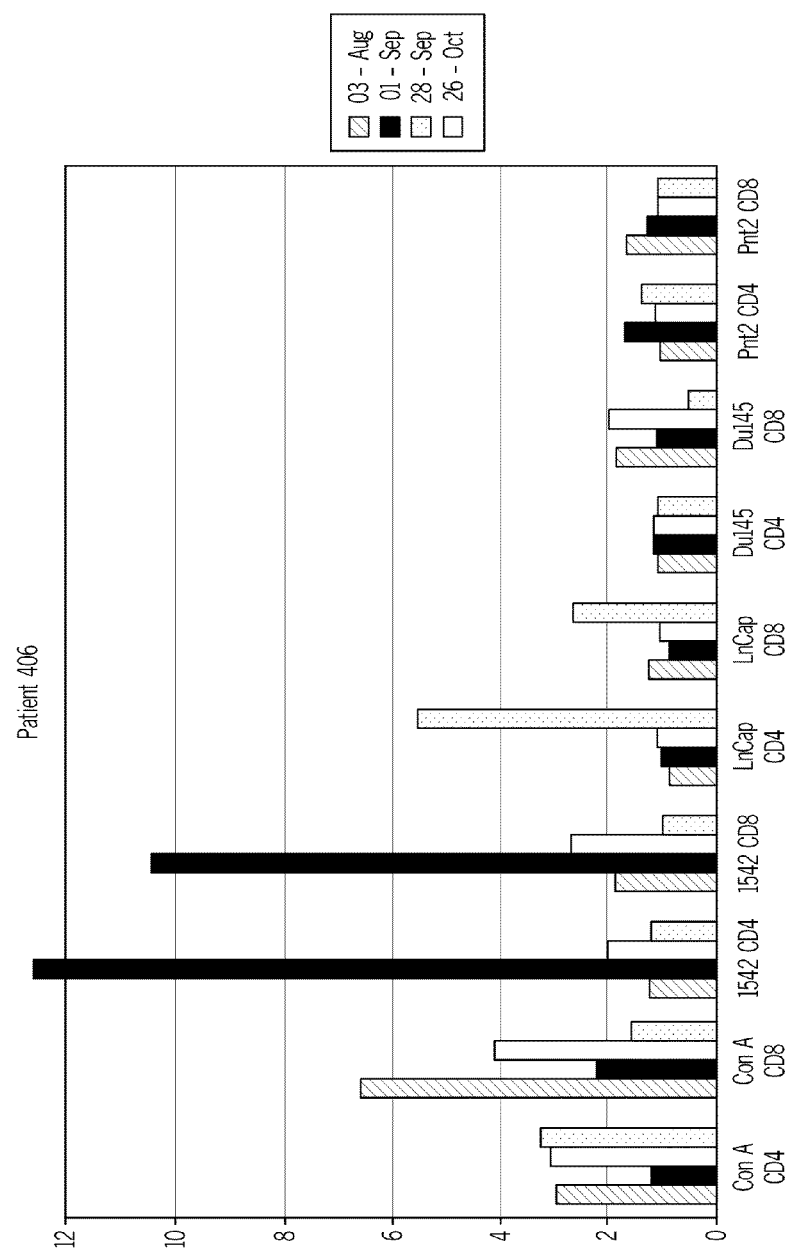
FIG. 1 shows a plot of proliferation index for various cell lysates.
Figure 2A:
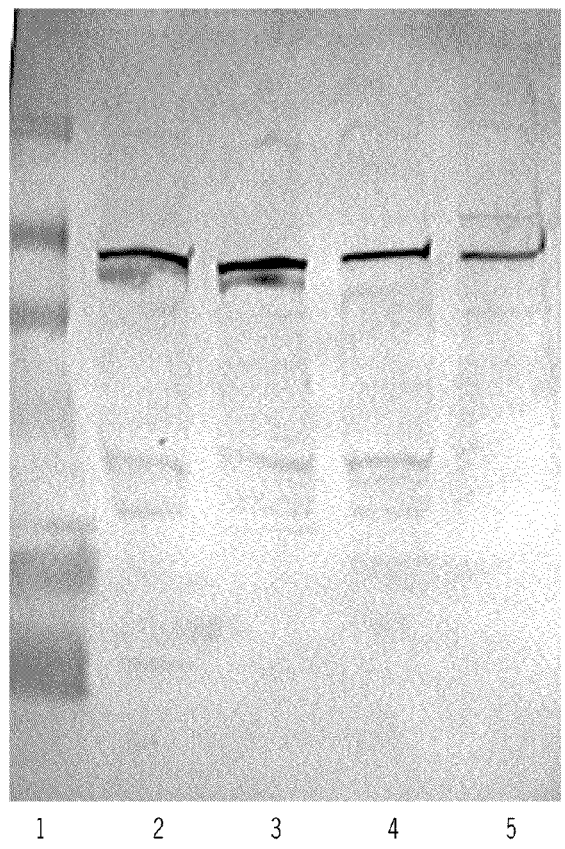
FIGS. 2A-2B, 2C-2D, and 2E-2F show Western Blot analyses of serum from patients 115, 304, and 402, respectively.
Figure 2B:
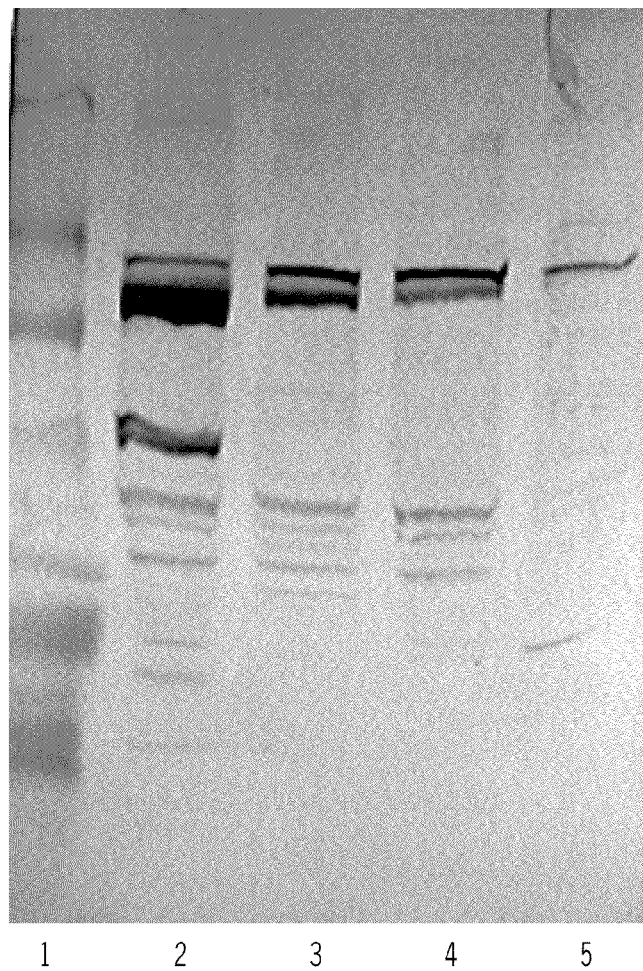
Figure 2C:
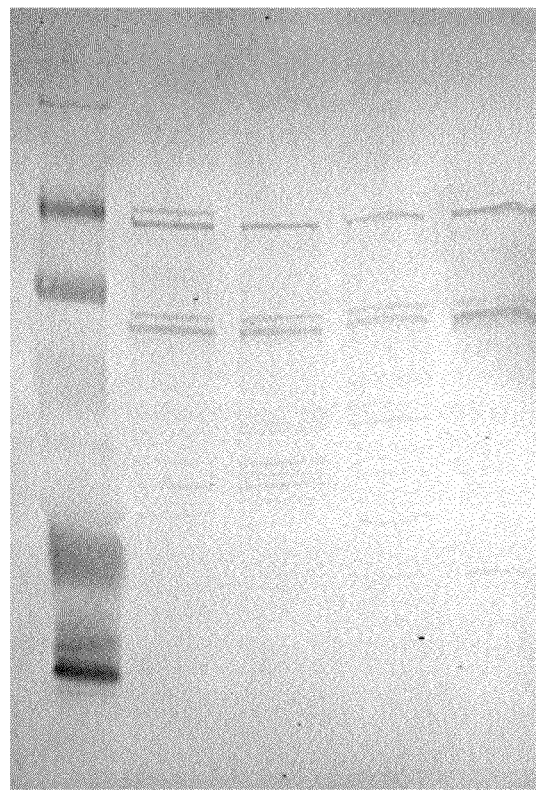
Figure 2D:
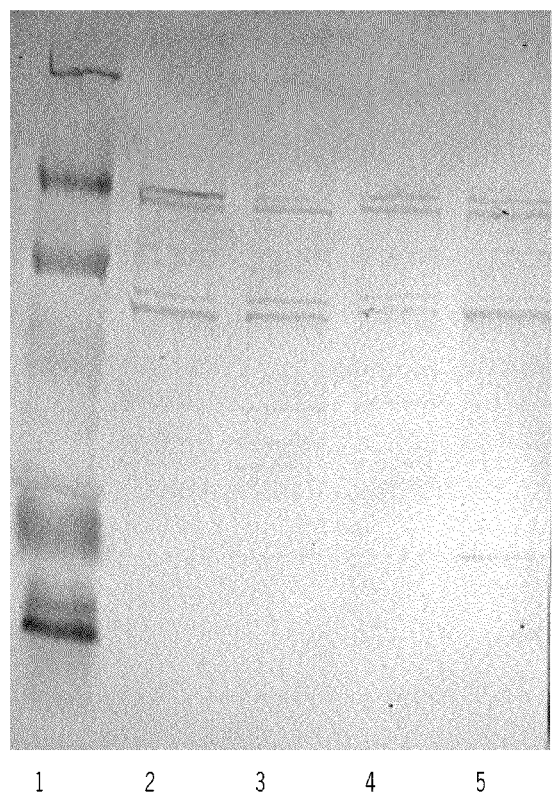
Figure 2E:
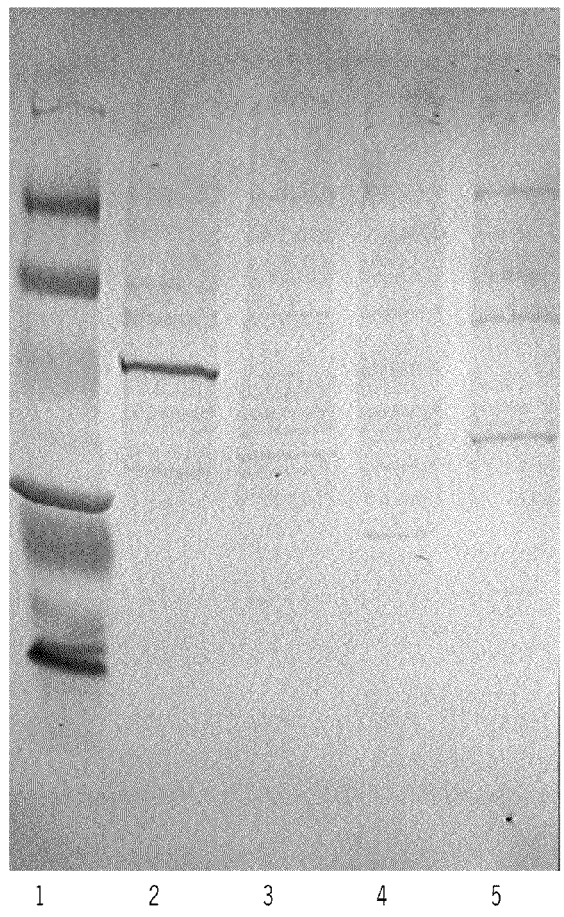
Figure 2F:
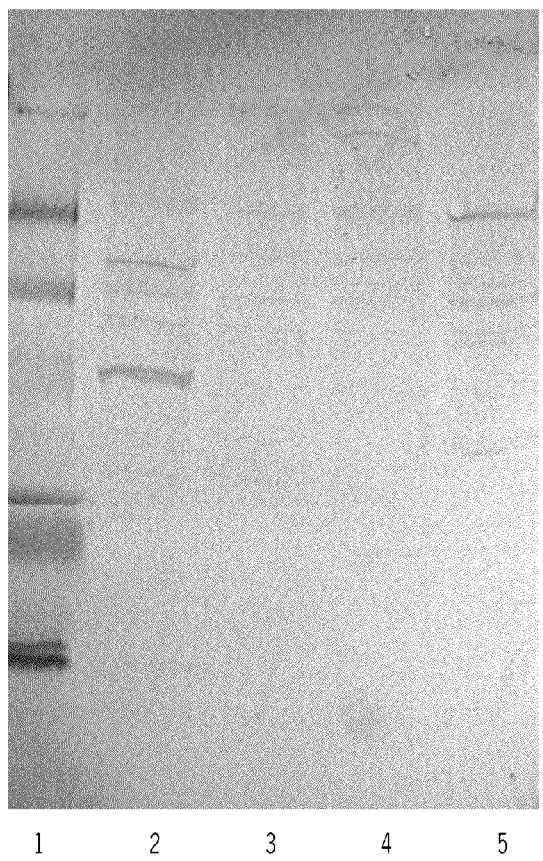

Generally, cell-based cancer vaccines until now have a common feature of employing cells that contain at least some TSAs and/or TAAs that are shared with antigens present in a patient's tumour. In each case, tumour cells are utilized as the starting point on the premise that only tumour cells will contain TSAs or TAAs of relevance, and the tissue origins of the cells are matched to the tumour site in patients.

In contrast to this expectation in the field, some embodiments of the invention utilize immortalized 'normal,' non-malignant cells as a basis of allogeneic cell cancer vaccines. Normal cells are not expected to posses TSAs or relevant concentrations of TAAs. Hence it was surprising that normal cells, and particularly combinations of normal cells with cells derived from tumour biopsies as described herein are effective as anti-cancer vaccines. The approach is general and can be adapted to any mammalian tumour by the use of immortalized normal cells derived from the same particular tissue as the tumour intended to be treated. Immortalized normal cells can be prepared by those skilled in the art using published methodologies, or they can be sourced from cell banks such as ATCC or ECACC, or they are available from several research groups in the field.

A prostate cancer vaccine, for example may include one or a combination of different immortalized normal cell lines derived from the prostate and can be prepared using methods reviewed and cited in Rhim, J. S. and Kung, H-F., 1997 Critical Reviews in *Oncogenesis* 8(4):305-328 or selected from PNT1A (ECACC Ref. No. 95012614), PNT2 (ECACC Ref. No. 95012613) or PZ-HPV-7 (ATCC No. CRL-2221). In an embodiment, a clonal derivative of PNT-2, named Ony-Cap-23 (ECACC Ref. No. 00032801) desirably is combined with cells obtained from primary or metastatic cancer biopsies. Accordingly, a further embodiment is the addition of TSAs and/or TAAs by combining one or more immortalized normal cell line(s) such as OnyCap-23 with one, two three or more different cell lines derived from primary and/or metastatic cancer biopsies. In an embodiment, prostate cancer cells from at least one cell line derived from a metastasis biopsy from lymph node, bone, brain or liver tissue are combined with at least one cell line derived from a biopsy of unmetastasised tissue from a prostate. In a particularly favourable embodiment, the metastasised sample derived cell line is LnCaP (ATCC No. CRL-1740) and the cell line from a primary prostate cancer biopsy is P4E6 (ECACC Ref. No. 04071601. Also, see Maitland et al., *Radiation Research* 155: 133-142 (2001). The compositions of these cell lines may further include cells or cell lines.

In another embodiment pursuant to the strategy of combining cells from a normal tissue cell line with other cells from at least two identifiable stages of cancer progression, cells from a normal prostate cell line are combined with at least one cell line representative of non-metastasised cells and at least one cell line representative of metastasised cells.

In an embodiment preferably cells from the LnCaP and P4E6 cell lines are combined with cells from a normal prostate cell line (such as OnyCap-23). The LnCaP and P4E6 cells in such formulations may be replaced or supplemented with cells from other cell lines that are derived from lymph node metastases or primary prostate cancers respectively may replace the LnCaP cells. Other cell lines representative of normal prostate cells may replace OnyCap-23, such as, for example, PNT-2 cells (see Maitland et al., *Radiation Research* 155: 133-142 (2001).

In yet another embodiment, a prostate cell line obtained from a tumour biopsy that exhibits high neutral endopeptidase-24.11 activity and low endothelin-converting enzyme activity (for example, as determined using the methods of Usmani et al., the relevant passages of which are particularly incorporated by reference) may replace the LnCaP cells. In yet another embodiment, a prostate cell line obtained from a tumour biopsy that exhibits low levels of both neutral endopeptidase-24.11 and endothelin-converting enzyme may replace the P4E6 cells. In another embodiment, other cell lines representative of normal prostate cells may replace OnyCap-23, such as, for example, PNT-2 cells.

In yet another embodiment, a vaccine comprises allogeneic cells from a first normal prostate cell line, allogeneic cells from a second immortalized cell line obtained from a prostate cancer biopsy that express normal levels of neutral endopeptidase but low levels of endothelin converting enzyme, and allogeneic cells from a third immortalized line obtained from a prostate cancer biopsy that express low levels of both neutral endopeptidase and endothelin converting enzyme. In this instance, the presence of tumour associated glycoprotein related to sialyated Tn antigen, as described by the work of Brenner et al. (see *J. Urology* 153: 1575-1579 1995) may be used to select a cell line obtained from a the primary prostate cancer. The differential presentation of neutral endopeptidase-24.11 and endothelin converting enzyme as described by Usmani et al. in *Clin. Science* 103 (supp 48): 3145-3175 can be used for this embodiment.

All the cell lines described herein will show good growth in large scale cell culture and sufficient characterization to allow for quality control and reproducible production.

Preferably, the cell lines are lethally irradiated utilizing gamma irradiation at 20-400 Gy to ensure that they are replication incompetent prior to use in the mammal or human.

The cell lines and combinations referenced herein preferably are frozen, freeze dried or otherwise stabilized to allow their transportation and storage. Accordingly, in a further embodiment a combination of cells referenced herein may be formulated with a cryoprotectant solution. Suitable cryoprotectant solutions may include but are not limited to, 10-30% v/v aqueous glycerol solution, 5-20% v/v dimethyl sulphoxide or 5-20% w/v human serum albumin may be used either as single cryoprotectants or in combination.

Cells obtained from the cell lines may be mixed in any convenient proportion. Preferably, no cell type is present in the mixture more than 20 fold (measured using total amounts of DNA) more than any other cell type. More preferably the ratio is less than 10, 5 or 3 fold.

Yet a further embodiment is the use of a cell line combination with a non-specific immune stimulant such as BCG, M. Vaccae, a *Mycobacterium*, Tetanus toxoid, *Diphtheria* toxoid, *Bordetella Pertussis*, interleukin 2, interleukin 12, interleukin 4, interleukin 7, Complete Freund's Adjuvant, Incomplete Freund's Adjuvant or another known non-specific agent. Such general immune stimulants advantageously can enhance immune status whilst the combinations of cell lines, contribute to immune enhancement via haplotype mismatch and, at the same time, target an immune response to a plethora of TAA and TSA due to their heterogeneity.

The invention is further described by the following examples, which do not limit the invention in any manner.

EXAMPLES

Example 1

Growth, Irradiation, Formulation and Storage of Cells

An immortalised cell line derived from normal prostate tissue namely PNT2 was grown in roller bottle culture in RPMI 1640 media supplemented with 2 mM L-glutamine and 5% fetal calf serum (FCS) following recovery from liquid nitrogen stocks. Following expansion in T175 static flasks the cells were seeded into roller bottles with a growth surface area of 850 cm$^2$ at 1-20×10$^7$ cells per roller bottle.

An immortalized cell line derived from primary prostate tissue namely NIH1542-CP3TX (ATCC No. CRL-12037) was grown in roller bottle culture in KSFM media supplemented with 25 µg/ml bovine pituitary extract, 5 ng/ml of epidermal growth factor, 2 mM L-glutamine, 10 mM HEPES buffer and 5% fetal calf serum (FCS) (hereinafter called "modified KSFM") following recovery from liquid nitrogen stocks. Following expansion in T175 static flasks the cells were seeded into roller bottles with a growth surface area of 1,700 cm$^2$ at 2-5×10$^7$ cells per roller bottle.

Two secondary derived cell lines, LnCap (ATCC No. CRL-1740) and Du145 (HTB-81), obtained from ATCC were used. LnCap was grown in large surface area static flasks in RPMI media supplemented with 10% FCS and 2 mM L-glutamine following seeding at 1-10×10$^6$ cells per vessel and then grown to near confluence. Du-145 was expanded from frozen stocks in static flasks and then seeded into 850 cm$^2$ roller bottles at 1-20×10$^7$ cells per bottle and grown to confluence in DMEM medium containing 10% FCS and 2 mM L-glutamine. All cell lines were harvested utilising trypsin at 1× normal concentration. Following extensive washing in DMEM the cells were re-suspended at a concentration of 5-40×10$^6$ cells/ml and irradiated at 50-300 Gy using a Co$^{60}$ source. Following irradiation the cells were formulated in cryopreservation solution composing of 10% DMSO, 8% human serum albumin in phosphate buffered saline, and frozen at a cell concentration of 5-150×10$^6$ cells/ml, in liquid nitrogen until required for use.

Vaccination Schedule

Prostate cancer patients were selected on the basis of being refractory to hormone therapy with a serum PSA level of at least 30 ng/ml.

| | Cell Lines Administered | | |
|---|---|---|---|
| Dose | Trial Arm A | Trial Arm B | Trial Arm C |
| 1, 2 and 3 | PNT2 | Du145 | LnCap |
| 4 and subsequent | PNT2/Du145/ NIH1542 | PNT2/Du145/ LnCap | PNT2/NIH1542/ LnCap |

The cells were warmed gently in a water bath at 37° C. and admixed with mycobacterial adjuvant prior to injection into patients. Injections were made intra-dermally at four injection sites into draining lymph node basins. The minimum interval between doses was two weeks, and most of the doses were given at intervals of four weeks. Prior to the first dose, and prior to some subsequent doses, the patients were tested for delayed-type hypersensitivity (DTH) against the four cell lines listed in the vaccination schedule above (all tests involved $0.8 \times 10^6$ cells with no adjuvant).

Immunological responses were analysed. T-Cell proliferation responses were determined as follows. To evaluate the expansion of T-cell populations that recognize antigens of the vaccinating cell lines, a T cell proliferation assay was used that employed stimulation with lysates from the prostate cell lines. Whole blood was extracted at each visit to the clinic and used in a BrdU (bromodeoxyuridine) based proliferation assay as described below:

| Patient BrdU proliferation method | | |
|---|---|---|
| Reagents | | |
| RPMI | | Life Technologies, Paisley, Scotland |
| BrdU | | Sigma Chemical Co, Poole, Dorset |
| PharMlyse | 35221E | Pharmingen, Oxford UK |
| Cytofix/Cytoperm | 2090KZ | " |
| Perm/Wash buffer (x10) | 2091KZ | " |
| FITC Anti-BrdU/Dnase | 340649 | Becton Dickinson |
| PerCP Anti-CD3 | 347344 | " |
| Pe Anti-CD4 | 30155X | Pharmingen |
| Pe Anti-CD8 | 30325X | " |
| FITC mu-IgG1 | 349041 | Becton Dickinson |
| PerCP IgG1 | 349044 | " |
| PE IgG1 | 340013 | " |

In this method, 1 ml blood is diluted with 9 ml RPMI+2 mM L-gln+PS+50 μM 2-Me. Serum should not be added. The blood is left overnight at 37° C. The following morning, 450 μl of diluted blood were aliquoted into wells of a 48-well plate and 50 μl of stimulator lysate added. The lysate was made by freeze-thawing tumour cells ($2 \times 10^6$ cell equivalents/ml)×3 in liquid nitrogen and then stored aliquots frozen until required. Cells are cultured at 37° C. for 5 days. On the evening of day 5 50 μl BrdU at 30 μg/ml are added. One hundred μl of each sample are aliquoted each into cells of a 96-well round-bottomed plate. Each plate is spun and supernatant discarded. Red cells are lysed using 100 μl Pharmlyse for 5 minutes at room temperature, and then washed ×2 with 50 μl of Cytofix. The samples are spun and supernatant removed by flicking. Then the cells are permeabilized with 100 μl Perm wash for 10 mins at RT. Thirty microliters of antibody mix are added, that comprise antibodies at correct dilution made up to volume with Perm-wash. The mixtures are incubated for 30 mins in the dark at room temperature. This is followed by wash ×1 and resuspension in 100 μl 2% paraformaldehyde. This is added to 400 μl FACSFlow in cluster tubes ready for analysis. Analysis is carried out with a FACScan, and storing 3000 gated CD3 events.

The set ups of microtiter plate conditions are shown in Table 1 and Table 2.

TABLE 1

| 6-well plate for stimulation. | | | | | |
|---|---|---|---|---|---|
| | Nil | ConA | 1542 | LnCap | Du145 | Pnt2 |
| PBL 1 | | | | | | |
| PBL 2 | | | | | | |
| PBL 3 | | | | | | |
| PBL 4 | | | | | | |
| PBL 5 | | | | | | |
| PBL 6 | | | | | | |

The results for the proliferation assays are shown in FIG. 1, wherein a proliferation index for either CD4 or CD8 positive T-cells are plotted against the various cell lysates. The proliferation indexes are derived by dividing through the percentage of T-cells proliferating by the no-lysate control.

Results are shown for three patients (numbers 112, 307 and 406). Results are given for four cell lysates namely, NIH1542, LnCap, DU-145 and PNT-2. Overall, 50% of patients treated mount a specific proliferative response to at least one of the cell lines.

Western blots using patient serum were carried out. Standardized cell lysates were prepared for a number of prostate cell lines to enable loading of similar quantities of protein on a denaturing SDS PAGE gel for Western blot analysis. Each blot was loaded with molecular weight markers, and equal amounts of protein derived from cell lysates of NIH1542, LnCap, DU-145 and PNT-2. The blot then was probed with serum from patients derived from pre-vaccination and following 16 weeks vaccination (four to six doses).

TABLE 2

| 96-well plate for antibody staining. | | | | | | | | | | | |
|---|---|---|---|---|---|---|---|---|---|---|---|
| PBL 1 | | PBL 2 | | PBL 3 | | PBL 4 | | PBL 5 | | PBL 6 | |
| Nil A | 15 D | Nil A | 15 D | Nil A | 15 D | Nil A | 15 D | Nil A | 15 D | Nil A | 15 D |
| Nil D | 15 E | Nil D | 15 E | Nil D | 15 E | Nil D | 15 E | Nil D | 15 E | Nil D | 15 E |
| Nil E | Ln D | Nil E | Ln D | Nil E | Ln D | Nil E | Ln D | Nil E | Ln D | Nil E | Ln D |
| Con D | Ln E | Con D | Ln E | Con D | Ln E | Con D | Ln E | Con D | Ln E | Con D | Ln E |
| Con E | Du D | Con E | Du D | Con E | Du D | Con E | Du D | Con E | Du D | Con E | Du D |
| | Du E | | Du E | | Du E | | Du E | | Du E | | Du E |

TABLE 2-continued 96-well plate for antibody staining.

| Pn D | Pn D | Pn D | Pn D | Pn D | Pn D |
| Pn E | Pn E | Pn E | Pn E | Pn E | Pn E |

Table Legend:
A:     IgG1-FITC (5 µl)     IgG1-PE (5 µl)     IgG1-PerCP (5 µl)
       15 µlMoAb + 15 µl)
D:     BrdU-FITC (5 µl)     CD4-PE (5 µl)     CD3-PerCP (5 µl)
       15 µlMoAb + 15 µl
E:     BrdU-FITC (5 µl)     CD8-PE (5 µl)     CD3-PerCP (5 µl)
       15 µlMoAb + 15 µl
15:    NIH1542-CP3TX
Ln:    LnCap
D:     Du1145
Pn:    PNT2
Con:   ConA lectin (positive control)
Nil:    No stimulation In this method, of sample preparation from prostate tumour lines, cell pellets are washed 3 times in PBS, and then re-suspended at $1 \times 10^7$ cells/ml of lysis buffer. The re-suspended cells are passed through 5 cycles of rapid freeze thaw lysis in a liquid nitrogen/water bath. The cells then are centrifuged at 1500 rpm for 5 minutes to remove cell debris, and ultracentrifuged at 20,000 rpm for 30 min to remove membrane contaminants. These are aliquoted at 200 µl and stored at −80° C. Gel electrophoresis is carried out by mixing lysates 1:1 with Laemelli sample buffer and boiling for 5 minutes. Then, 20 µg samples are loaded into 4-20% gradient gel wells. The sample gels are electrophoresed in to Bjerrum and Schafer-Nielson transfer buffer (with SDS) at 200 V for 35 minutes.

Western transfer methods were carried out by equilibrating gels, nitrocellulose membranes and blotting paper in transfer buffer for 15 minutes. Western blot data from serum of patients 115, 307, and 406 are presented as FIGS. 2A-2B, 2C-2D, and 2E-2F, respectively. Then gel-nitrocellulose sandwiches are arranged on anodes of semi-dry electrophoretic transfer cells made from 2 sheets of blotting paper, nitrocellulose membrane, gel, and 2 sheets of blotting paper. A cathode is applied and sandwiches exposed to 25 V for 90 minutes. Immunological detection of proteins was carried out by blocking nitrocellulose membranes overnight at 4° C. with 5% Marvel in PBS/0/05% Tween 20. The membranes were rinsed twice in PBS/0.05% Tween 20, then wash for 20 min and 2×5 min at RT on a shaking platform. The membranes were then incubated in 1:20 dilution of clarified patient plasma for 120 min at RT on a shaking platform. This was followed by a wash as above with an additional 5 min final wash. The membranes were then incubated in 1:250 dilution of biotin anti-human IgG of IgM for 90 min at RT on a shaking platform, then washed as above with an additional 5 min final wash. Then the membranes are incubated in 1:1000 dilution of streptavidin-horseradish peroxidase conjugate for 60 min at RT on a shaking platform, and washed as above. The membranes are then incubated in Diaminobenzidine peroxidase substrate for 5 min to allow colour development. The reaction is stopped by rinsing the membranes with water.

Figure 3A:
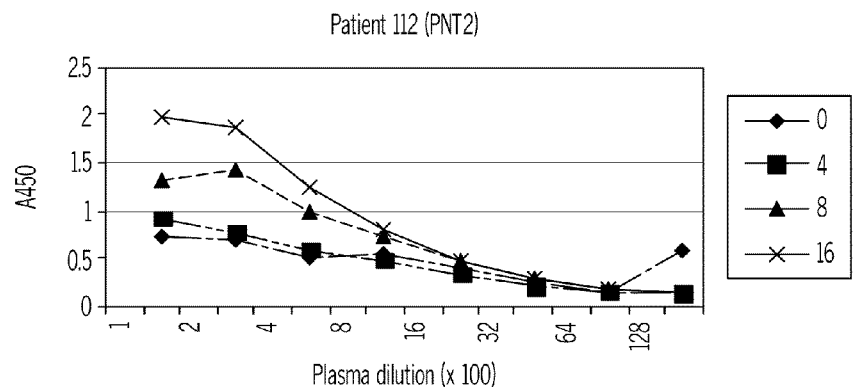
FIGS. 3A, 3B, and 3C show antibody titres of serum from three patients.
Figure 3B:
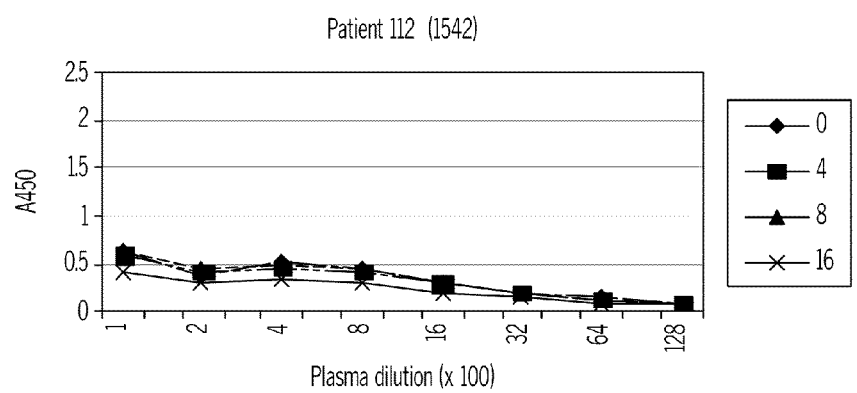
Figure 3C:
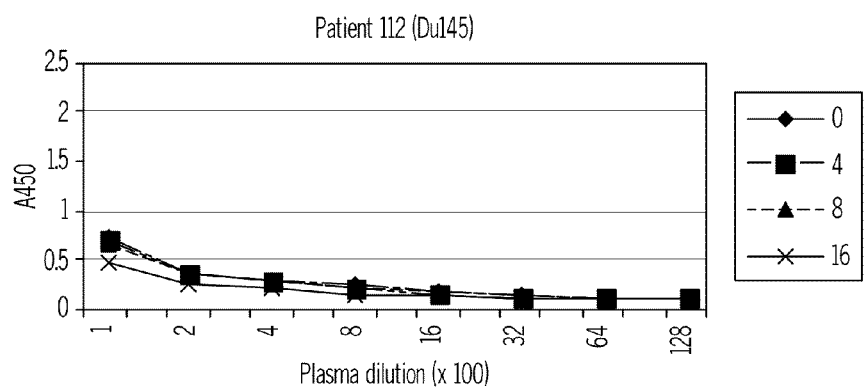
Figure 3D:
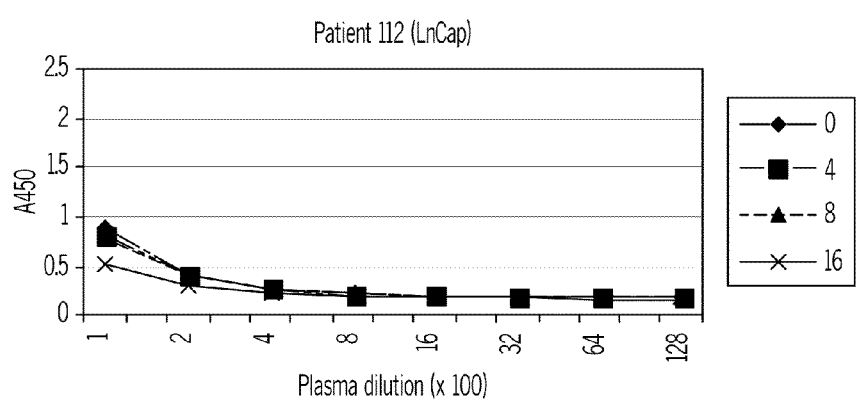
Figure 3E:
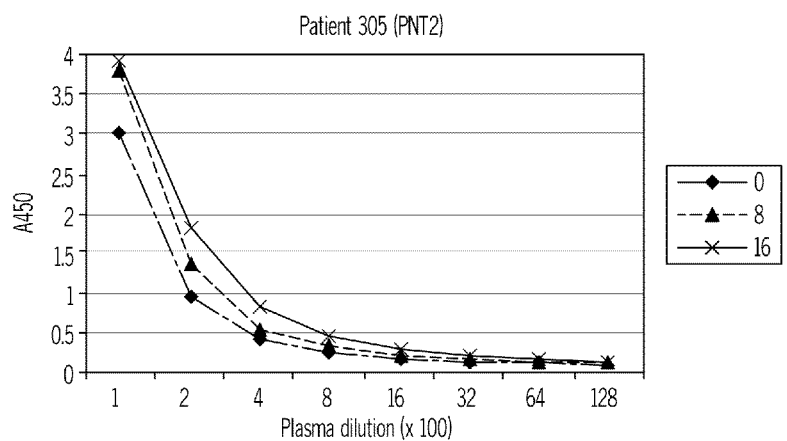
Figure 3F:
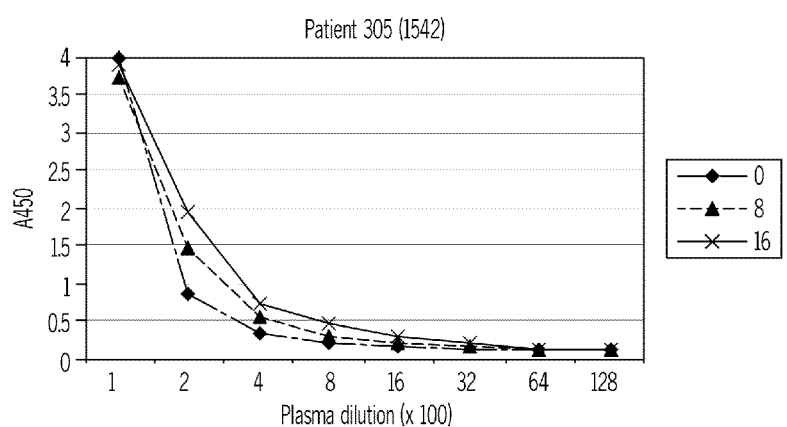
Figure 3G:
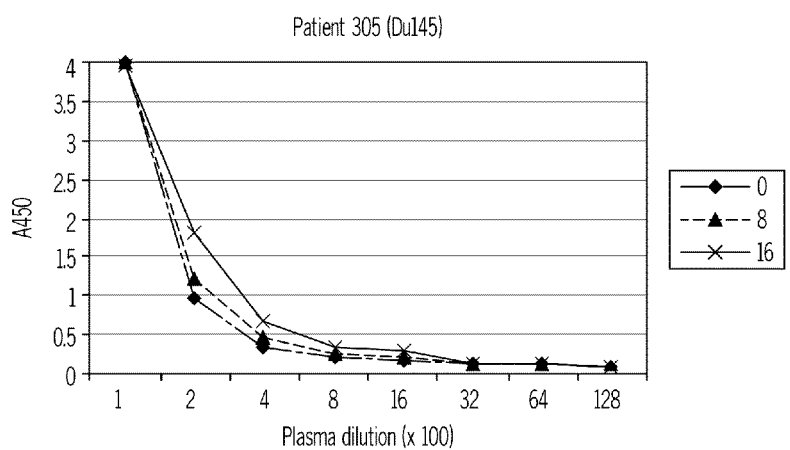
Figure 3H:
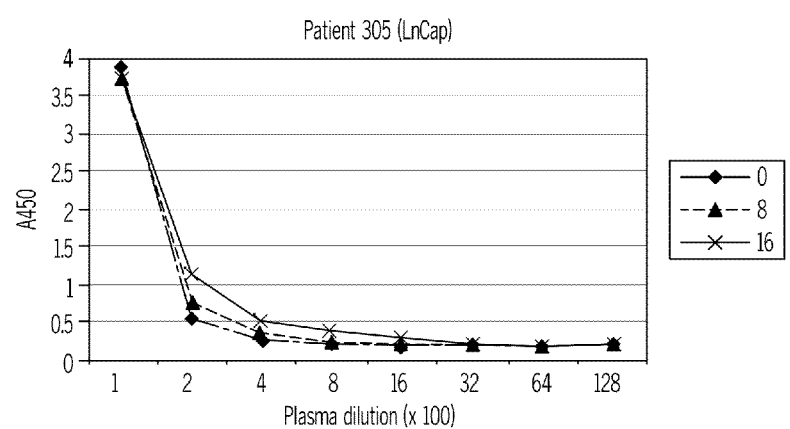
Figure 3I:
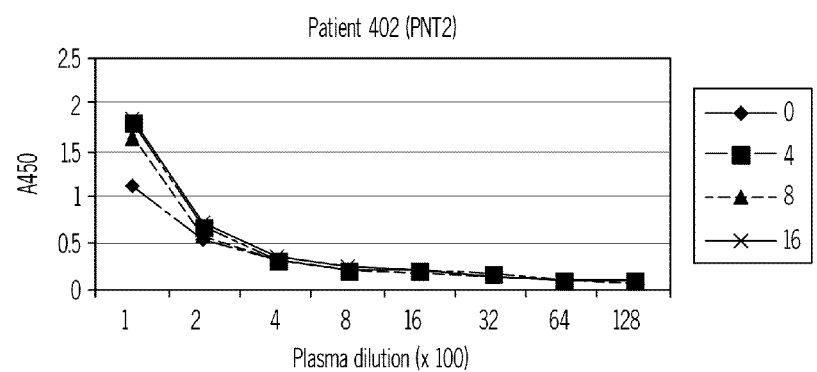
Figure 3J:
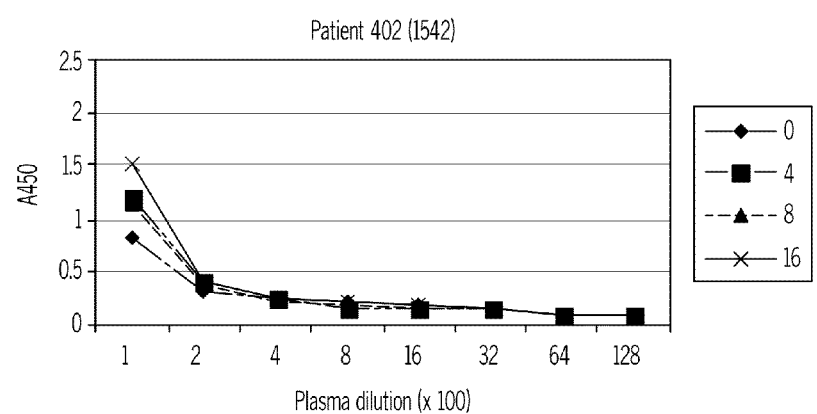
Figure 3K:
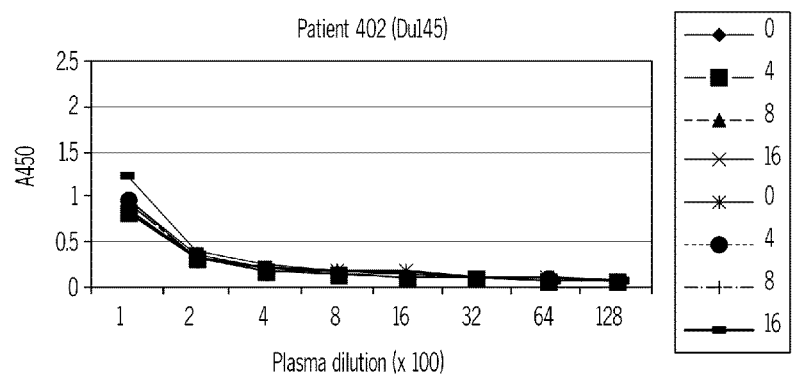
Figure 3L:
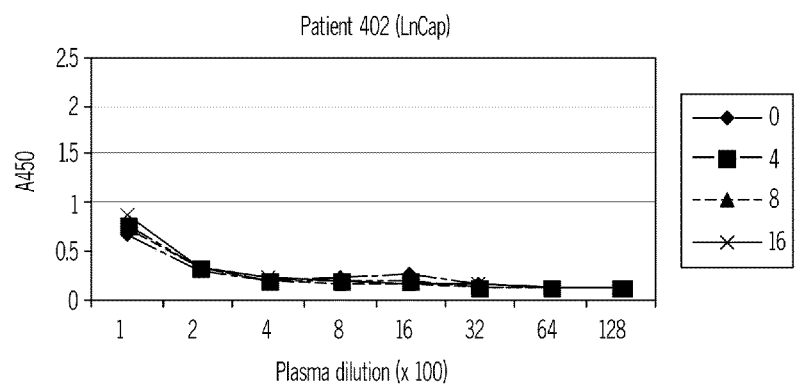

FIGS. 3A, 3B, and 3C show 3 results obtained from three patients (112, 305, and 402, respectively). These results show clearly that vaccination over a 16 week period, using four to six doses, can cause an increase in antibody titre against cell line lysates as well as cross reactivity against lysates not received in this vaccination regime (other than DTH testing).

Antibody titres were determined by coating ELISA plates with standardised cell line lysates and by dilution studies on serum from vaccinated patients. The Elisa method utilized anti-lysate IgG. Plates were coated with 50 µl/well lysates at 10 µg/ml according to dilutions in the following Table 3.

TABLE 3

Dilution Table.

| Lysate | Protein conc | Coating conc | Amount/ml | Amount |
| --- | --- | --- | --- | --- |
| PNT2 | 2.5 mg/ml | 10 µg/ml | 3.89 µl | 19.4 µl |
| 1542 | 4.8 mg/ml | 10 µg/ml | 2.07 µl | 10.3 µl |
| Du145 | 2.4 mg/ml | 10 µg/ml | 4.17 µl | 20.8 µl |
| LnCap | 2.4 mg/ml | 10 µg/ml | 4.12 µl | 20.6 µl |

Each sample was covered and incubate overnight at 4° C., followed by wash ×2 with PBS-Tween. Each plate was pounded on paper towels to dry and then samples blocked with PBS/10% FCS (100 µl/well). These were covered and incubate at room temperature (RT) for 1 hour (minimum) and then wash ×2 with PBS-Tween. Then 100 µl PBS-10% FCS were added to samples in rows 2-8, 200 µl plasma samples (diluted 1 in 100 in PBS-10% FCS that is, 10 µl plasma added to 990 µl PBS-10% FCS) to row 1 and serial 100 µl dilutions made down the plate below the row. The extra 100 µl from bottom wells were discarded and each plate covered and incubated in a refrigerator overnight.

Biotinylated antibody solution (Pharmingen; IgG 34162D) was diluted and added i.e. final concentration 1 mg/ml (i.e. 20 ml in 10 mls). The samples were covered and incubated at RT for 45 minutes and washed ×6 as above. A dilute streptavidin −HRP conjugate obtained from Pharmingen, (13047E 0) was diluted 1:1000 (i.e. 10 ml→10 mls) and added to 100 ul/well. The samples were incubated at 30 min at RT and then wash ×8. Then 100 µl substrate solution was added to each well and signal allowed to develop for 10-80 min at RT. The colour reaction was stopped by adding 100 ul M $H_2SO_4$ per well and the optical densities determined at 405 nm.

Results obtained indicated that, antibody titres at baseline (0), 4 weeks, 8 weeks and 16 weeks for the 3 patients (112, 305 and 402) increase. The data show that after vaccination with at least four doses, patients exhibit increased antibody titre against cell line lysates and also cross-reactivity against cell lines not received in this vaccination regime (except as DTH doses).

Figure 4A:
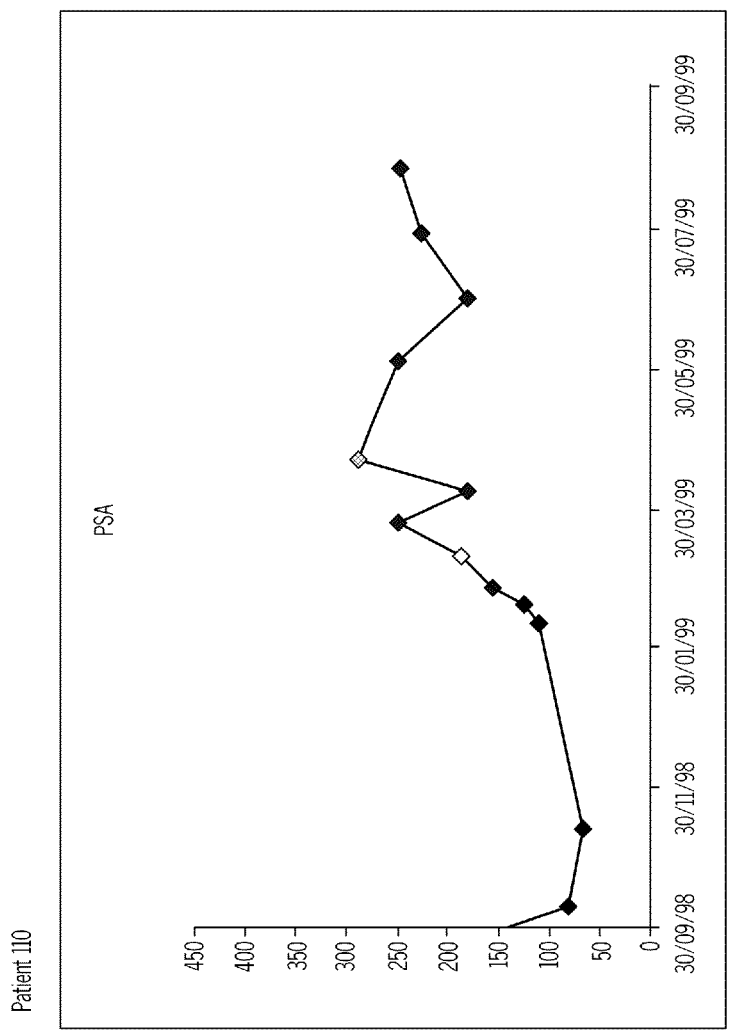
FIGS. 4A, 4B, and 4C show PSA values for three patients.
Figure 4B:
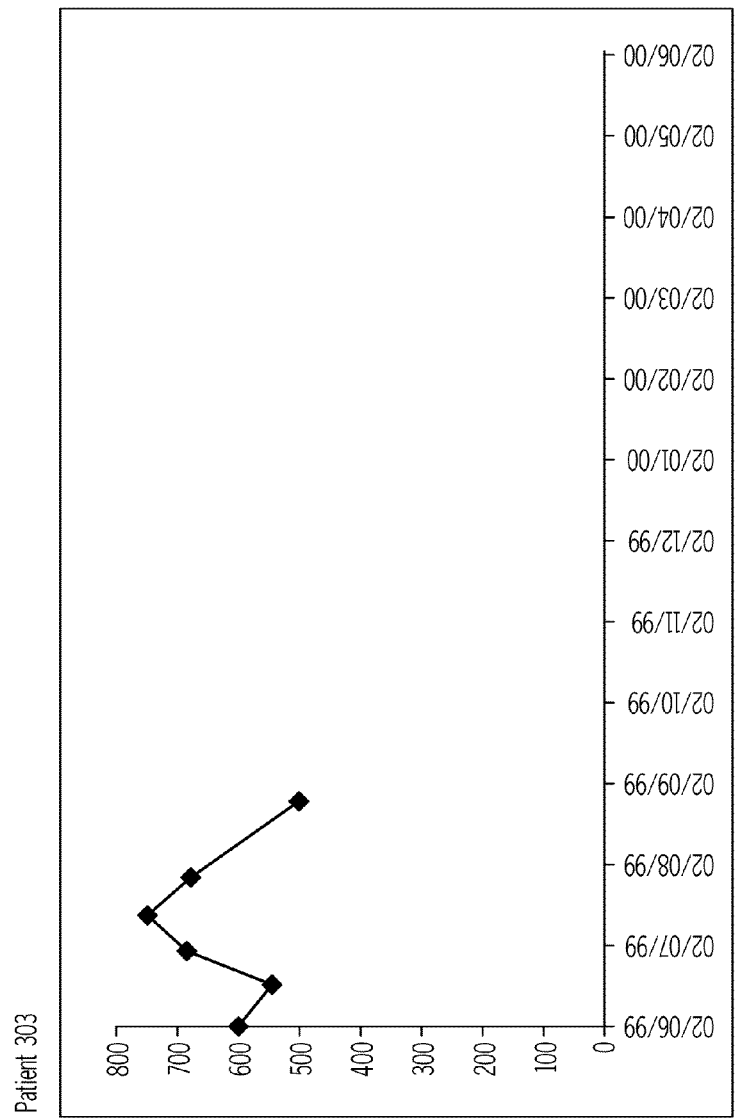
Figure 4C:
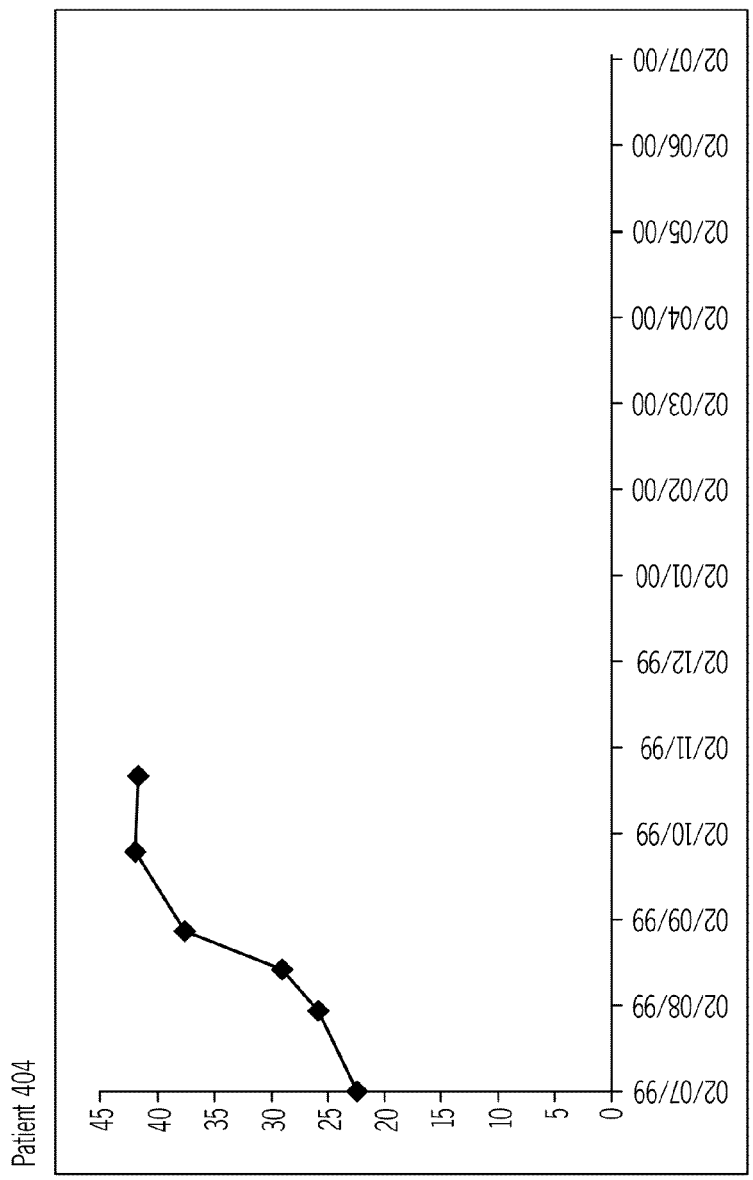

PSA levels were evaluated for patients receiving the vaccine at entry into the trial and throughout the course of vaccination, using routinely used clinical kits. The PSA values for three patients (110, 303, and 404) are shown in FIGS. 4A, 4B, and 4C, respectively (vertical axis is serum PSA in ng/ml;

horizontal axis is time, with the first time point representing the initiation of the vaccination programme) and portray a drop or partial stabilization of the PSA values, which in this group of patients normally continues to rise, often exponentially. The result for patient 110 is somewhat confounded by the radiotherapy treatment to alleviate bone pain, although the PSA level had dropped prior to radiotherapy.

Example 2

Use of a Normal Melanocyte in a Murine Melanoma Protection Model Model

Figure 5:
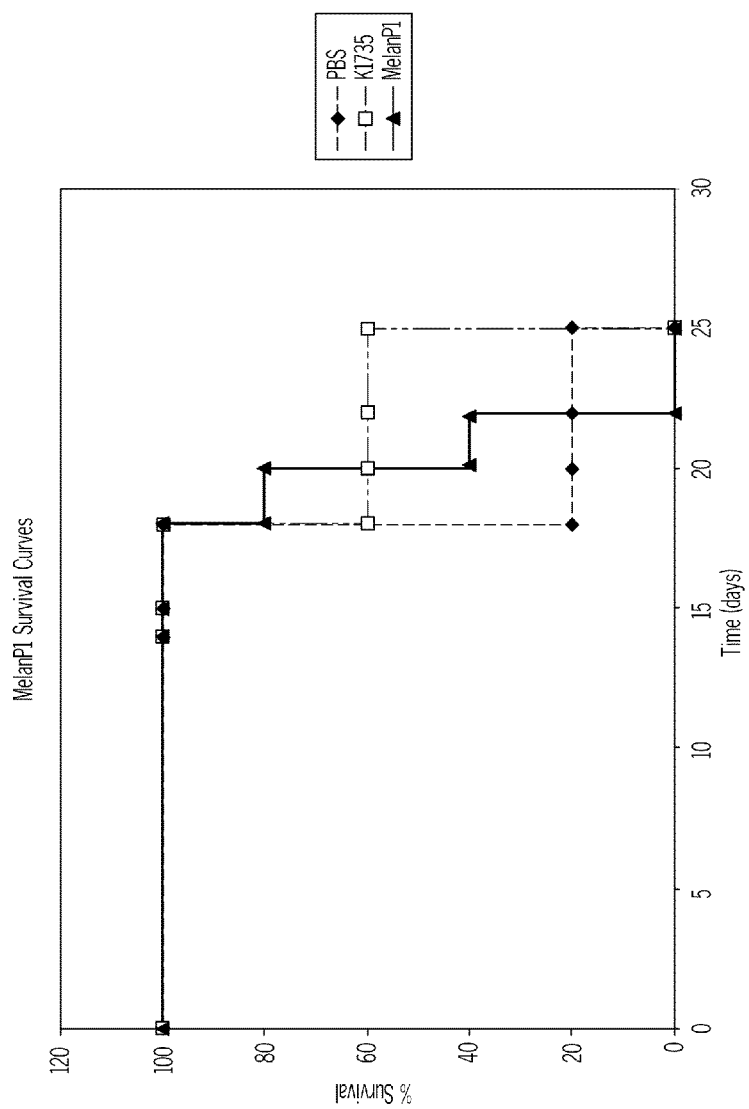
FIG. 5 shows survival curves for C57 mice immunized with normal melanocytes.

A normal melanocyte cell line was used in a vaccination protection model of murine melanoma utilising the B16.F10 as the challenge dose. The C57 mice received two vaccinations of either PBS, $5\times10^6$ irradiated KI735 allogeneic melanoma cells or $5\times10^6$ irradiated Melan P1 autologous normal melanocyte cells on days -14 and -7. Challenge on day 0 was with $1\times10^4$ B16.F10 cells and tumor volume measured every three days from day 10 onwards. Animals were sacrificed when the tumor had grown to 1.5×1.5 cm measured across the maximum dimensions of the tumor. It was found that that vaccination with Melan1P cells offer some level of protection against this particularly aggressive murine tumour, as seen in FIG. 5.

Example 3

Phase I/II Study

A phase I/II study was carried out with three types of allogeneic cells representing a normal prostate cell line, a prostate tumour derived cell line and a metastasised tumour cell line. A combined cell vaccine was given to patients having hormone refractory prostate cancer and safety, tolerability and efficacy, as measured by effect on survival and quality of life determined. The following criteria were used for inclusion of patients: patients of any age with histologically confirmed prostate cancer; patients with hormonal refractory disease following optimal first line LHRH treatment, or high dose bicalutamide (150 mg per day), or orchidectomy; progressive disease indicated by a rise in serum PSA on at least 2 successive occasions separated by at least 4 weeks; serum PSA level of at least 2 ng/ml at Week-2; WHO Performance Status of 0-2 at Week-4; a life expectancy of at least 6 months; the ability of the patient to read and understand the patient information leaflet and to give written informed consent; the willingness and ability of the patient to attend the hospital for all treatments and assessments; adequate bone marrow function (WBC>3500/mm$^3$, haemoglobin>9 g/dl, platelet count>100,000/mm$^3$ at Week 0); adequate renal function at Week 0 (serum creatinine<2.0 mg/dl); adequate hepatic function at Week 0 (<2 times upper limit of normal, ALT 52 U/l, AST 40 U/l); adequate response to DTH testing with the specified intra-dermal antigens at Week 0; and normal 24 hour Urinary Cortisol at Week-2 (60-240 nmol/24 hr).

The following criteria were used for removing a patient from the study. A patient could withdraw at any time without reason. The investigator could withdraw a patient if it is in the best interest of the patient. Commencement on any other investigational agent, radiotherapy, chemotherapy or corticosteroids (for example, in spinal cord compression) or surgical intervention was another criteria. Protocol violation by investigator or patient that in the opinion of the Sponsor's medical expert would interfere with the study was another. Unacceptable toxicity, disease progression as measured by appearance of new metastatic lesions confirmed by radiological investigations, and symptomatic disease progression also could prompt withdrawal. Patients who withdrew before completion of 6 months treatment with ONY-P1 were replaced unless withdrawal was due to disease progression or unacceptable toxicity.

An open label safety, tolerability and efficacy trial was carried out as follows. A combined vaccine "ONY-P1" was used in a translucent plastic Cryo Sleeve that contained three Greiner Cryo.S vials, each containing $8\times10^6$ irradiated cells. Each vial contained one of the following cell lines: Vial 1: LnCaP (Code CT3); Vial 2: P4E6 (Code CT4); Vial 3: Ony-Cap-23 (Code CT1). The vials were stored in the vapour phase of liquid nitrogen at -178° C. and transported to an investigational site on the day of administration in a Dewar Flask that contains liquid nitrogen. Cells were suspended in Hanks Balanced Salts Solution plus 2% foetal calf serum plus 8% dimethyl sulfoxide. BCG was obtained by Onyvax (OncoTICE, N.V. Organon, Kloosterstraat 6, PO Box 20, 5340 BH Oss, The Netherlands, PL 05003/0046) and each dose contained $0.6$-$2.4\times10^6$ CFU (the range stems from the product label). The product was diluted in saline for injection to yield the specified dose in 0.1 ml. Each injection suspension contained the contents of three complete vials (one of each cell type). The total volume (made up with the requisite volume of saline for injection) was 1 ml, given as 8×0.125 ml intradermal injections, with two injections into each draining lymph node basin. The BCG-adjuvanted doses were given at weeks 0 and 2; cells alone are given at weeks 4, 8, and at 4-weekly intervals up to and including week 48 (14 doses in total).

TABLE 4

Treatment Schedule.

| Activity | Week Number | | | | | | | | | | | | | |
|---|---|---|---|---|---|---|---|---|---|---|---|---|---|---|
| | -4 | -2 | 0 | 2 | 4 | 8 | 12 | 13 | 14 | 15 | 16 | 20 | 24 | 28 | 32 |
| PSA (10 ml)[1] | Y | Y | Y | Y | Y | Y | Y | | | | Y | Y | Y | Y | Y |
| Chemistry (10 ml)[2] | | Y | Y | Y | Y | Y | Y | | | | Y | Y | Y | Y | Y |
| Haematology (5 ml)[3] | | Y | Y | Y | Y | Y | Y | | | | Y | Y | Y | Y | Y |
| Immunology profile | Y | Y | Y | Y | Y | | Y | Y | Y | Y | Y | | | | Y |
| DTH Antigens | | Y | | | | | | | | | Y | | | | |
| DTH Cell Lines | | | | | Y | | | | | | Y | | | | |
| 24 h urinary cortisol | | Y | | | | | | | | | | | | | |
| Physical exam[5] | Y | | | | Y | Y | | | | | | Y | | | |
| Chest X-ray | | Y | | | | Y | | | | | | Y | | | |
| Bone scan | | Y | | | | | | | | | | Y | | | |
| CT abdomen/pelvis | | Y | | | | | | | | | | Y | | | |

TABLE 4-continued

Treatment Schedule.

| | | | | | | | | | | |
|---|---|---|---|---|---|---|---|---|---|---|
| EORTC QLQ-30 | Y | | | | | | Y | | | |
| Skin punch biopsy | | | Y | | | | Y | | | |
| BCG | Y | Y | | | | | | | | |
| ONY-P1 | Y | Y | Y | Y | Y | | Y | Y | Y | Y | Y |

| | Week Number | | | | | | | | | | |
|---|---|---|---|---|---|---|---|---|---|---|---|
| Activity | 33 | 34 | 35 | 36 | 40 | 44 | 48 | 49 | 50 | 51 | 52 |
| PSA (10 ml)[1] | | | | Y | Y | Y | Y | | | | Y |
| Chemistry (10 ml)[2] | | | | Y | Y | Y | Y | | | | Y |
| Haematology (5 ml)[3] | | | | Y | Y | Y | Y | | | | Y |
| Immunology profile | Y | Y | Y | Y | | | Y | Y | Y | Y | Y |
| DTH Antigens | | | | | | Y | | | | | Y |
| DTH Cell Lines | | | | | | Y | | | | | |
| 24 h urinary cortisol | | | | | | | | | | | |
| Physical exam[5] | | | | Y | | | | | | | Y |
| Chest X-ray | | | | Y | | | | | | | Y |
| Bone scan | | | | | | | | | | | Y |
| CT abdomen/pelvis | | | | | | | | | | | Y |
| EORTC QLQ-30 | | | | | | | | | | | Y |
| Skin punch biopsy | | | | | | Y | | | | | |
| BCG | | | | | | | | | | | |
| ONY-P1 | | | | Y | Y | Y | Y | | | | |

[1]Sample to be taken in Na-Heparin vacutainer. If sample taken on the same occasion as for Chemistry, then one 10 ml sample will suffice for both.
[2]Sample to be taken in Na-Heparin vacutainer. If sample taken on the same occasion as for Chemistry, then one 10 ml sample will suffice for both.
[3]Sample to be taken into EDTA.
[4]Samples to be taken in Na-Heparin. 10 ml volume to be taken on all occasions unless written request for 50 ml made by Sponsor.
[5]Including Physical/clinical assessment, vital signs and International Prostate Symptom Score.

The study was an open label design in a maximum of 48 evaluable patients split into two cohort groups. The first cohort group (cohort 1) was composed of 28 patients without bone metastases and the second cohort group (cohort 2) was composed of 20 patients with bone metastases. The total treatment period for each individual patient was 12 months. The three-stage study was as follows: i.) stage one, a pre treatment phase and an initial treatment phase lasting four weeks in which patients receive ONY-P1 plus BCG; ii) stage two, which lasted 48 weeks wherein patients were treated once a month with ONY-P1 alone; and iii) stage three, a follow up of all patients for 12 months following completion of treatment.

The treatment-assay schedule shown in Table 4 above was carried out.

In an initial analysis of the data, the first 15 patients who received more than 4 months of treatment were reviewed in great detail Of the 15, 5 showed statistically significant PSA velocity reductions. It was concluded that there were no safety issues, 5 of the 15 showed stabilization of PSA titres that correlated with their immunological profile (Th1/Th2).

PSA data from the clinical trial are presented by plotting each patient on a log scale. See FIGS. 6 through 8. Data taken prior to vaccination are shown in grey lines, which corresponds to the left side of the plot until the sustained increase in FIG. 6, and the first third of the plots of FIGS. 7 and 8 prior to levelling off. Data taken during vaccination is shown as later data points which are more levelled off. In hormone refractory prostate cancer the PSA level increases logarithmically until death. Certain existing therapies do show effects on PSA velocity, but these have been transient and not associated with effects on patient survival. At this disease stage, the PSA velocity either remains constant, or, as shown by patient 6 (non-responder) below, increases.

Figure 6:
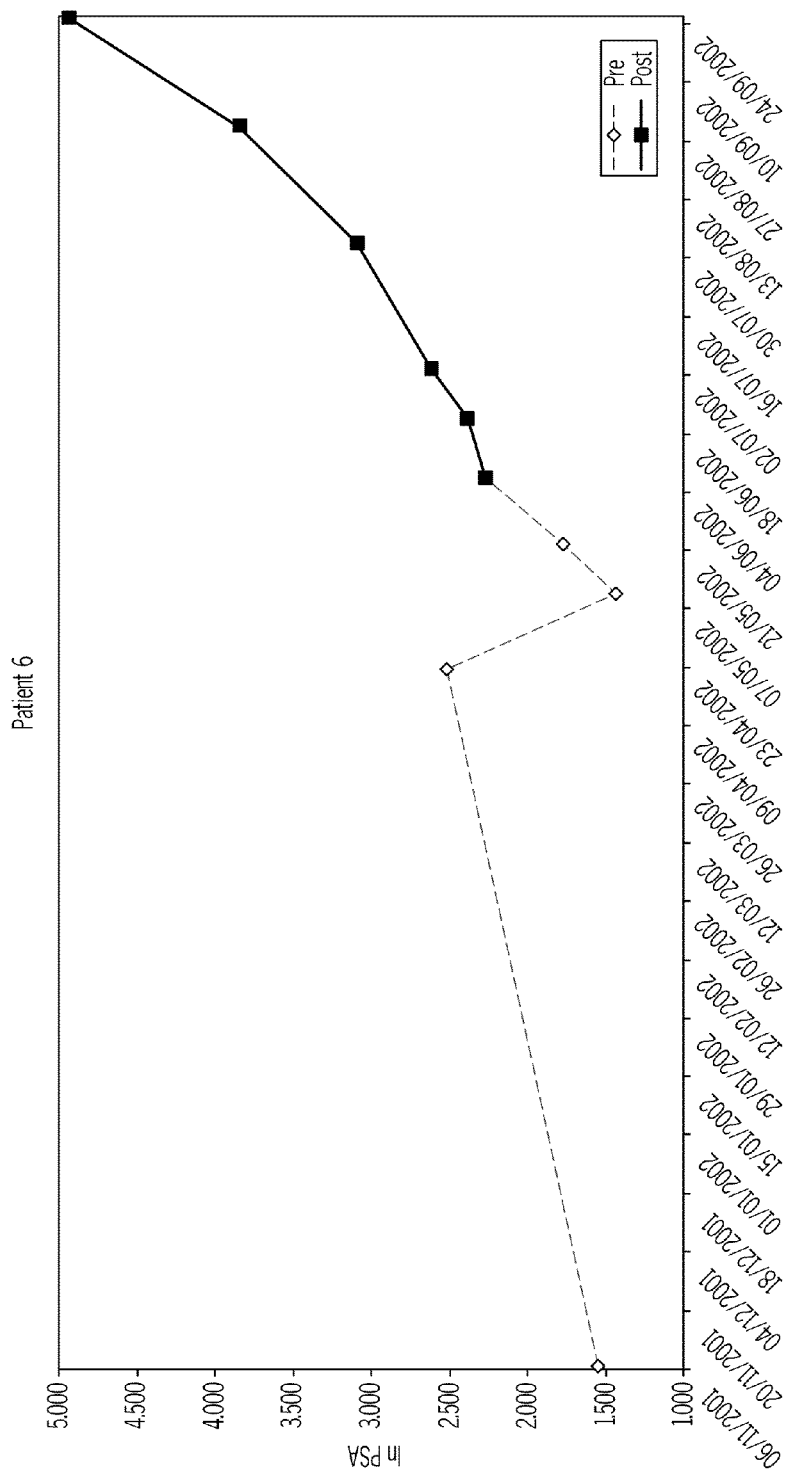
FIG. 6 shows a PSA level in a non-responding patient increasing logarithmically.
Figure 7:
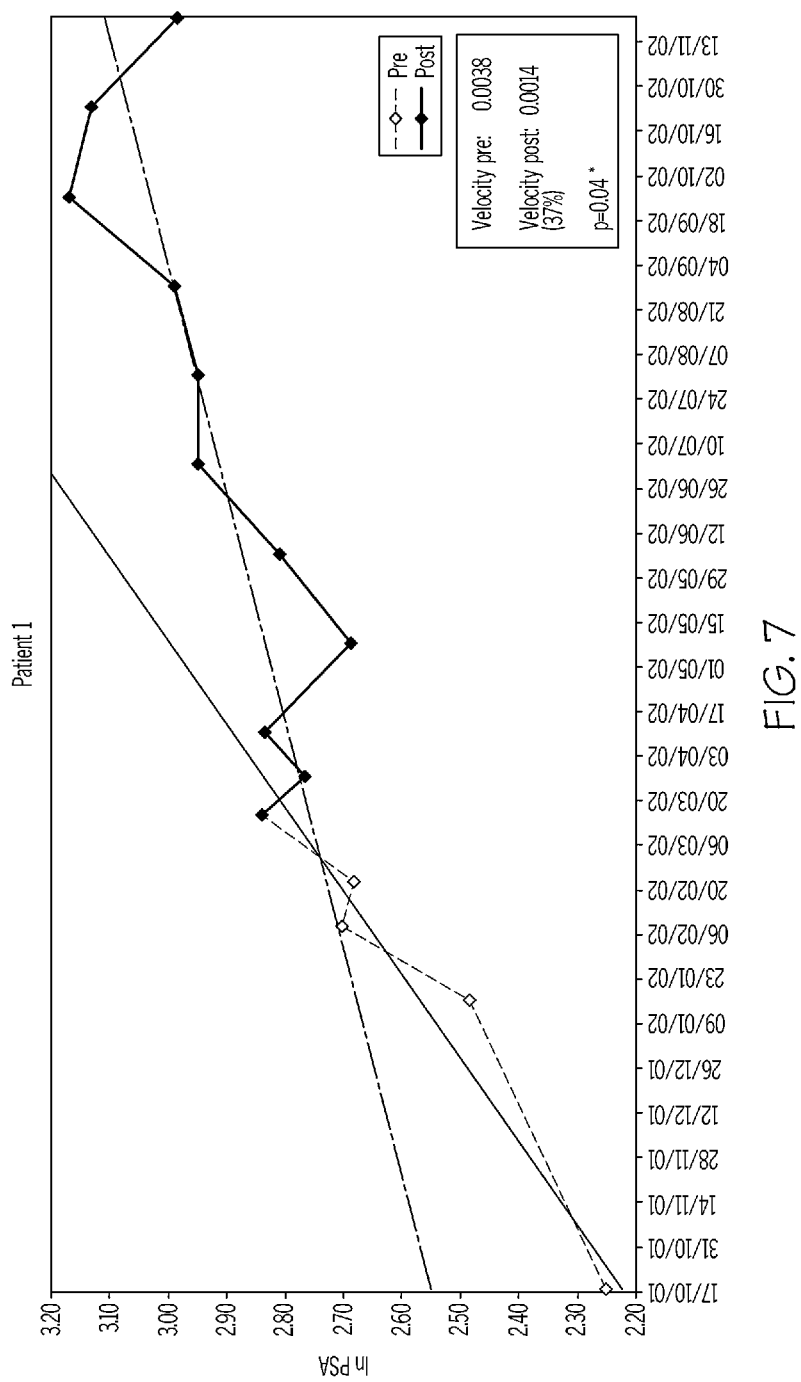
FIG. 7 shows reduction in the rate of PSA increase for a patient.
Figure 8:
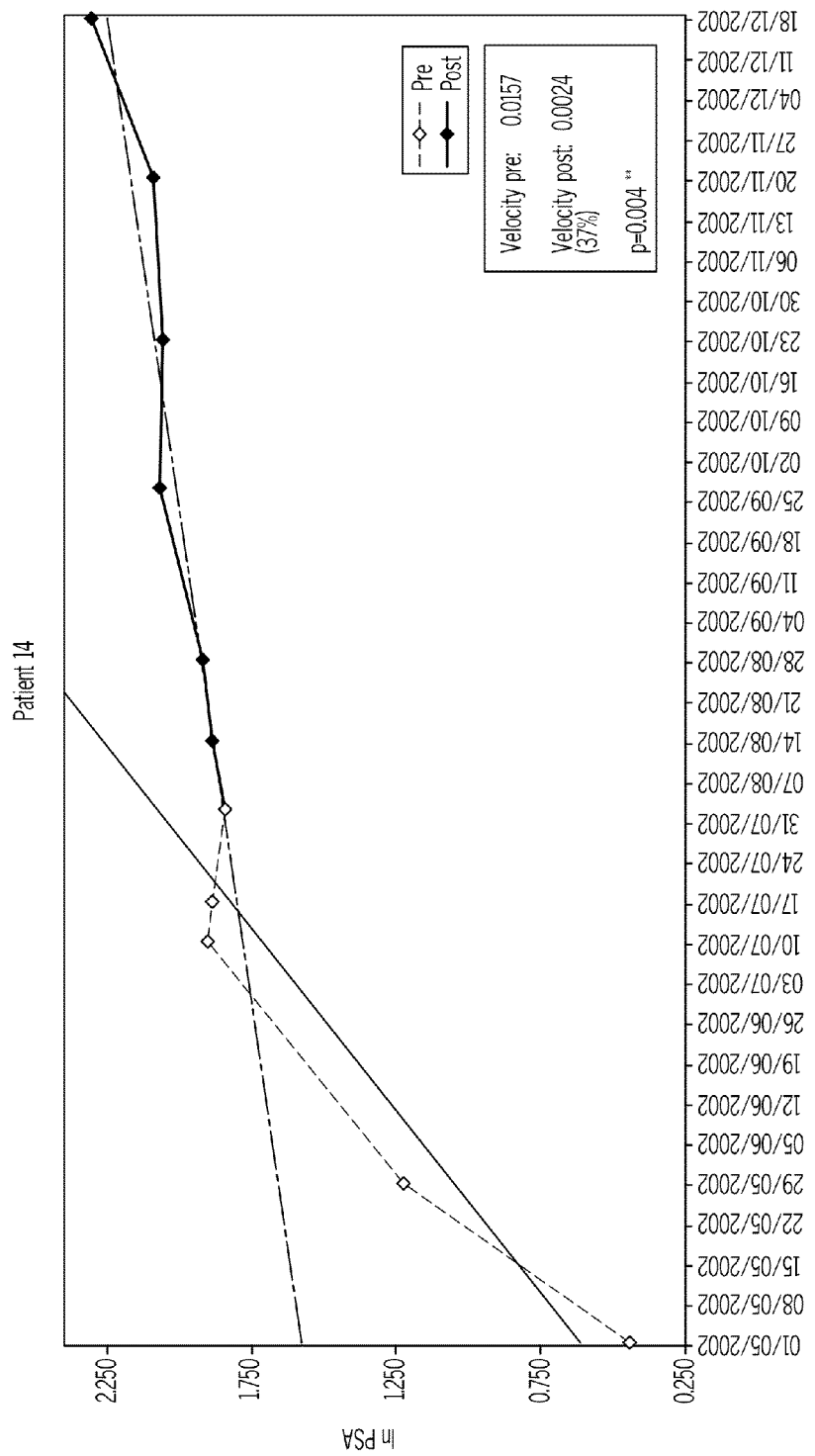
FIG. 8 shows reduction in the rate of PSA increase for a patient.

FIGS. 6 through 8 show PSA levels in individual patients, which increased logarithmically. A control, or non-responder as represented by patient results shown in FIG. 6 shows a PSA level that increases logarithmically until death. The y axis depicts In PSA concentration and the x axis depicts time over a year period.

Figure 10:
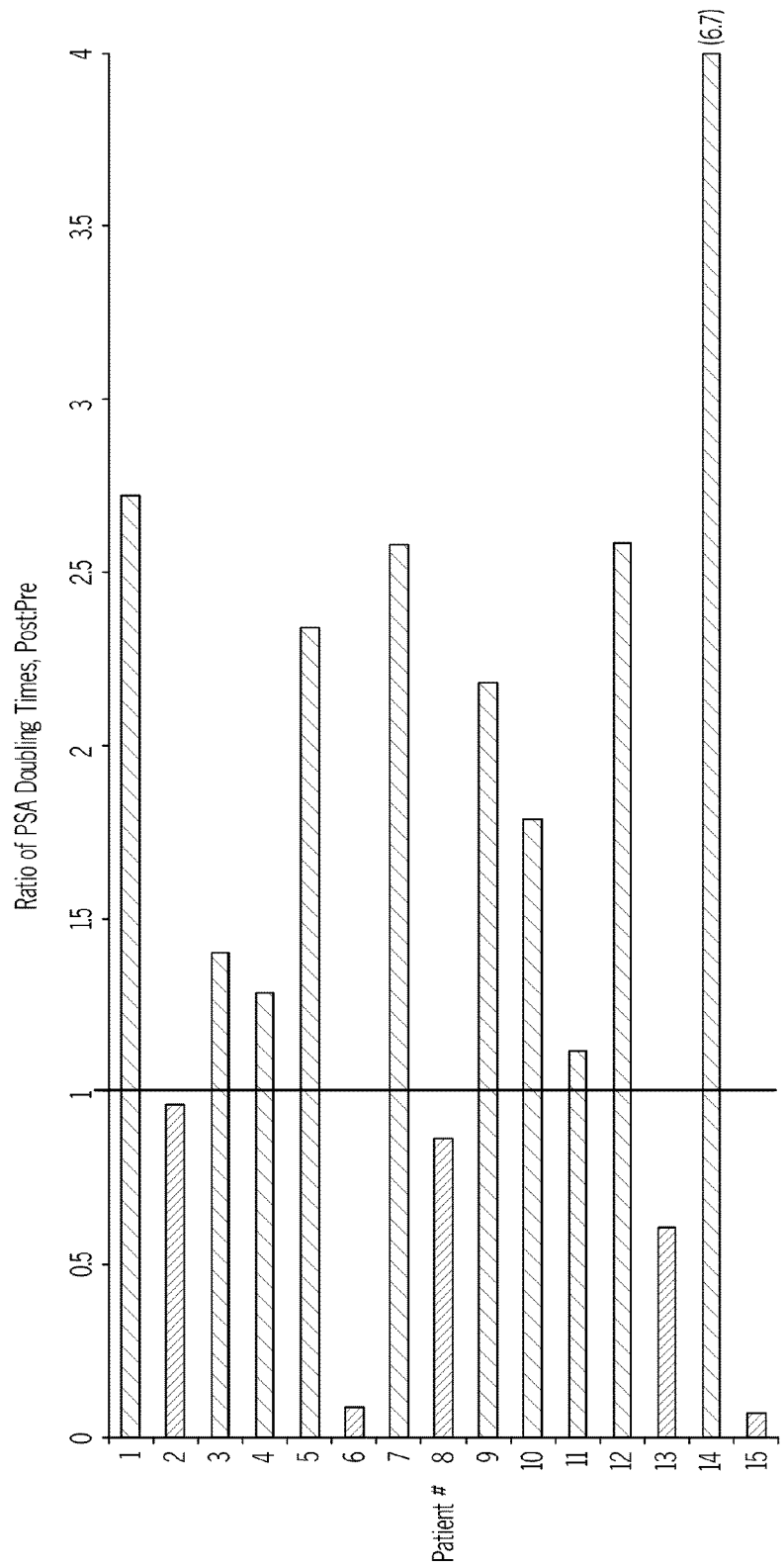
FIG. 10 shows the ratio of PSA doubling time for 15 patients.

Some typical existing therapies show effects on the "PSA velocity" as seen in the dip in the plot of FIG. 6, but such effects generally are transient and not associated with effects on patient survival. In contrast, five of the first 15 patients analysed, sustained statistically significant reductions in PSA velocity (for example, patients 1 and 14), the data of which are shown in FIGS. 7 and 8. The data to the left of the inflection mark show velocity prior to treatment and the data points to the right show the lower velocity after treatment. The straight lines from left to right indicate the linear regression of the data before and after treatment, respectively. More importantly, a decrease in velocity of PSA was seen equivalent to an increase in PSA doubling time, as summarized in FIGS. 9 and 10. FIG. 9 provides representative data from 15 patients and FIG. 10 depicts the ratio of PSA doubling times before and after treatment.

ONY-P1 Clinical Studies and PSA Data.

As described above, the study included 48 hormone-resistant prostate cancer (HRPC) patients split into two cohort groups. Vaccine composition and dosages also are described in Example 3. Cohort group 1 was composed of 28 patients with no bone metastases and cohort group 2 was composed of 20 patients with asymptomatic bone metastases. Twenty-six of 28 patients of the cohort group 1 and 13 of 20 patients from the cohort group 2 were treated. The remaining patients were excluded from the study for non-compliance with the study protocol. The total treatment period for each individual patient was 12 months with intradermal injections. The three-stage study was as follows: i) stage one, a pre treatment phase and an initial treatment phase lasting up to two weeks in which patients receive ONY-P1 plus BCG; ii) stage two, which lasted up to 4-48 weeks wherein patients were treated once a month with ONY-P1 alone; and iii) stage three, a follow up of all patients for 12 months following completion of treatment.

Figure 11:
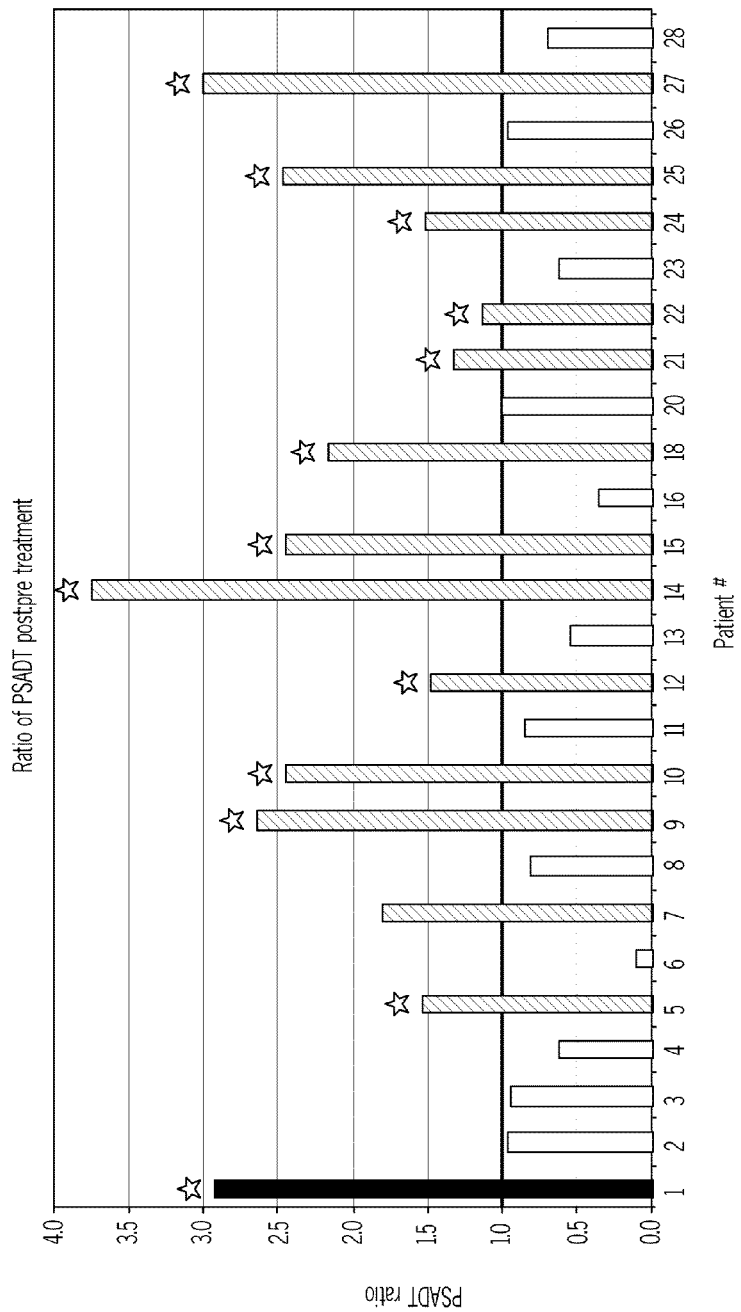
FIG. 11 shows the effect of ONY-P1 treatment on PSA doubling times (PSADT) of patients in cohort group 1 (cohort 1).

FIG. 11 shows the effect of ONY-P 1 treatment on PSA doubling times (PSADT) of patients in cohort group 1. All pre-treatment PSA data and the PSA data during the treatment were collated in a database. Natural log (In) PSA was plotted against time and the gradients of the plots corresponded to the PSA velocity (PSAV). PSADT was derived by the formula ln(2)/PSAV. The ratio of "on-treatment PSADT" to "pre-treatment PSADT" is shown in the FIG. 11. Ratios greater than 1 indicate an increase in PSADT induced by ONY-P1 therapy, and vice versa. It is known in the art that PSADT naturally decreases as HRPC progresses and generally, a spontaneous increase in PSADT is not observed. In FIG. 11, stars indicate patients in which the increased PSADT is statistically significant (p<0.05), as determined by multiple regression using a standard analysis on the Graph Pad Prism 3 computer programme.

Referring to FIG. 11, 11 out of the 26 treated patients of cohort group 1 exhibited statistically-significant increases in PSADT. By mathematical definition, this also means that the same 11 patients showed a statistically-significant reduction in PSAV. The mean increase in PSADT in the eleven patients was two-fold.

Figure 12:
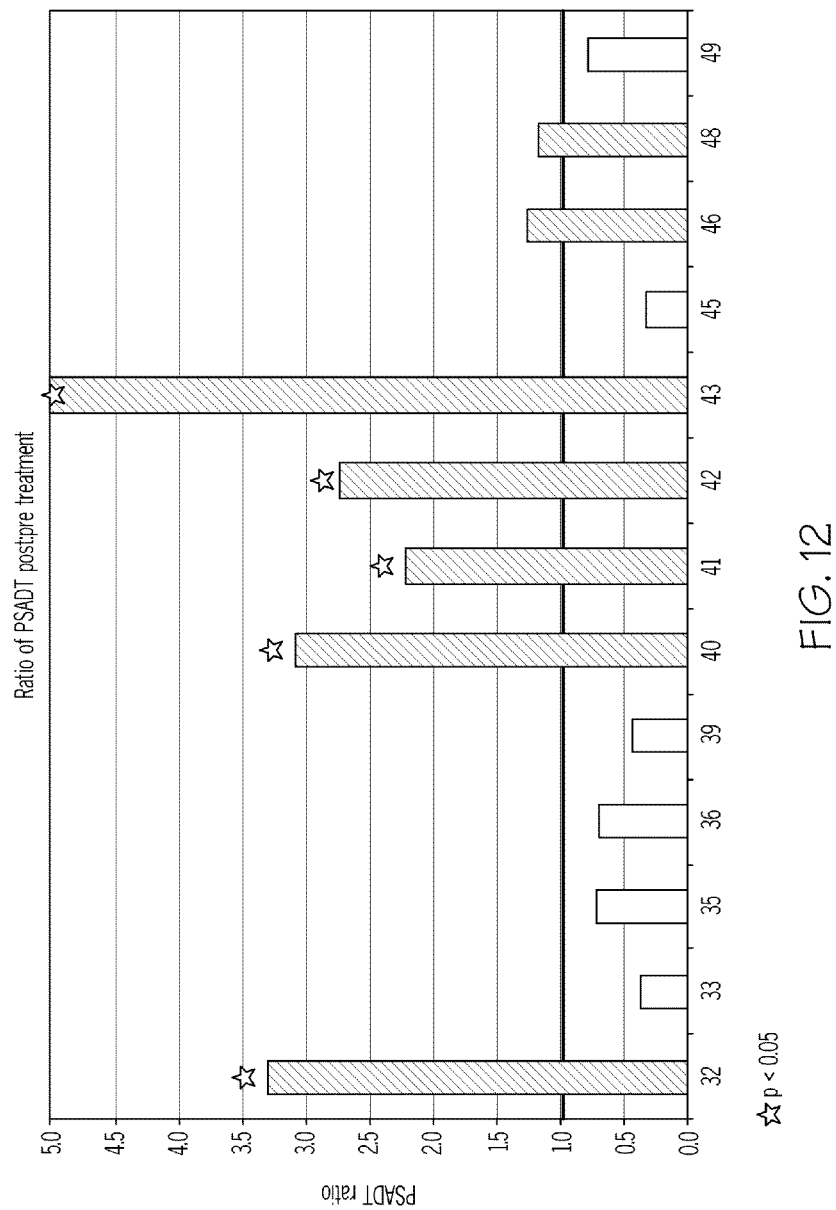
FIG. 12 shows the effect of ONY-P1 treatment on PSA doubling times (PSADT) of patients in cohort group 2 (cohort 2).

An equivalent analysis also was performed for patients in cohort group 2 and the results are depicted in FIG. 12. Five of the 13 treated patients in cohort group 2 showed a statistically-significant increase in PSADT as determined by the Graph Pad Prism 3 analysis (see FIG. 12). The mean increase in PSADT in the five patients was over three-fold.

Figure 13:
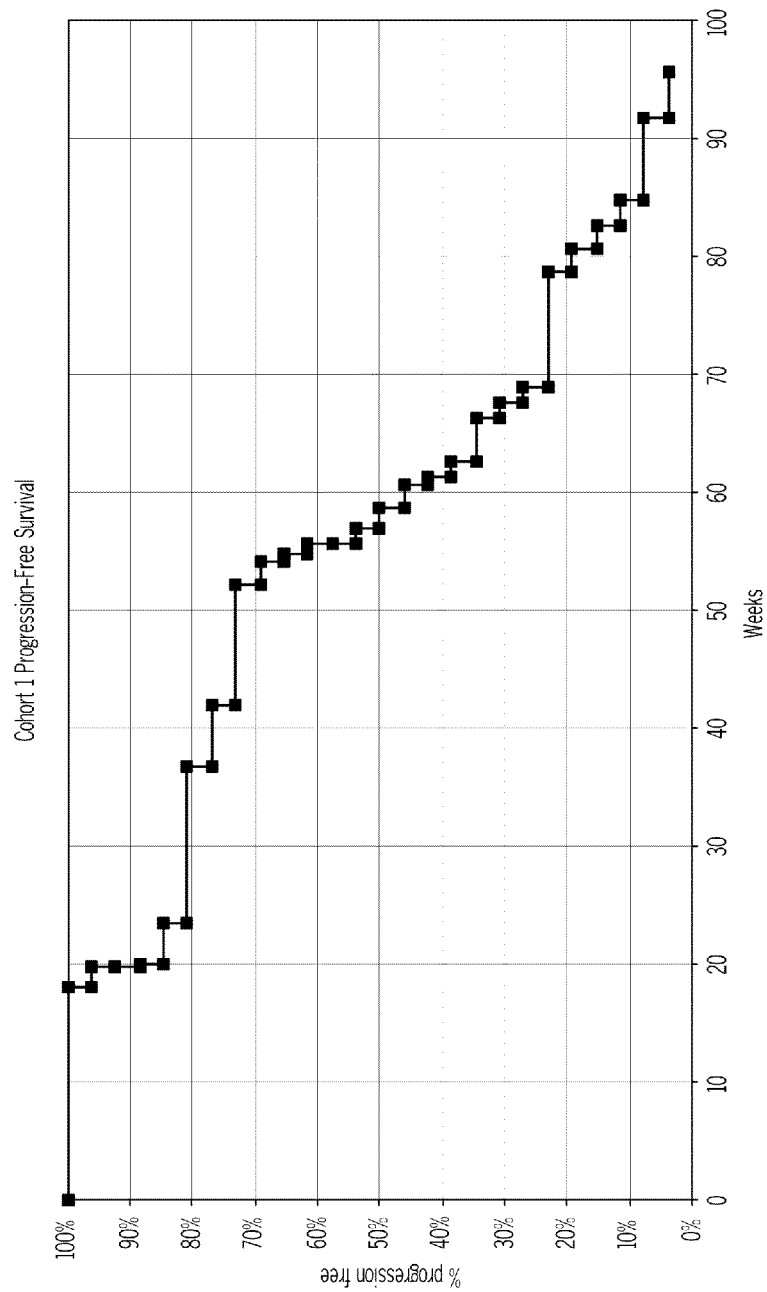
FIG. 13 depicts assessed time to disease progression (TTP) in patients of cohort group 1 (cohort 1).
Figure 14:
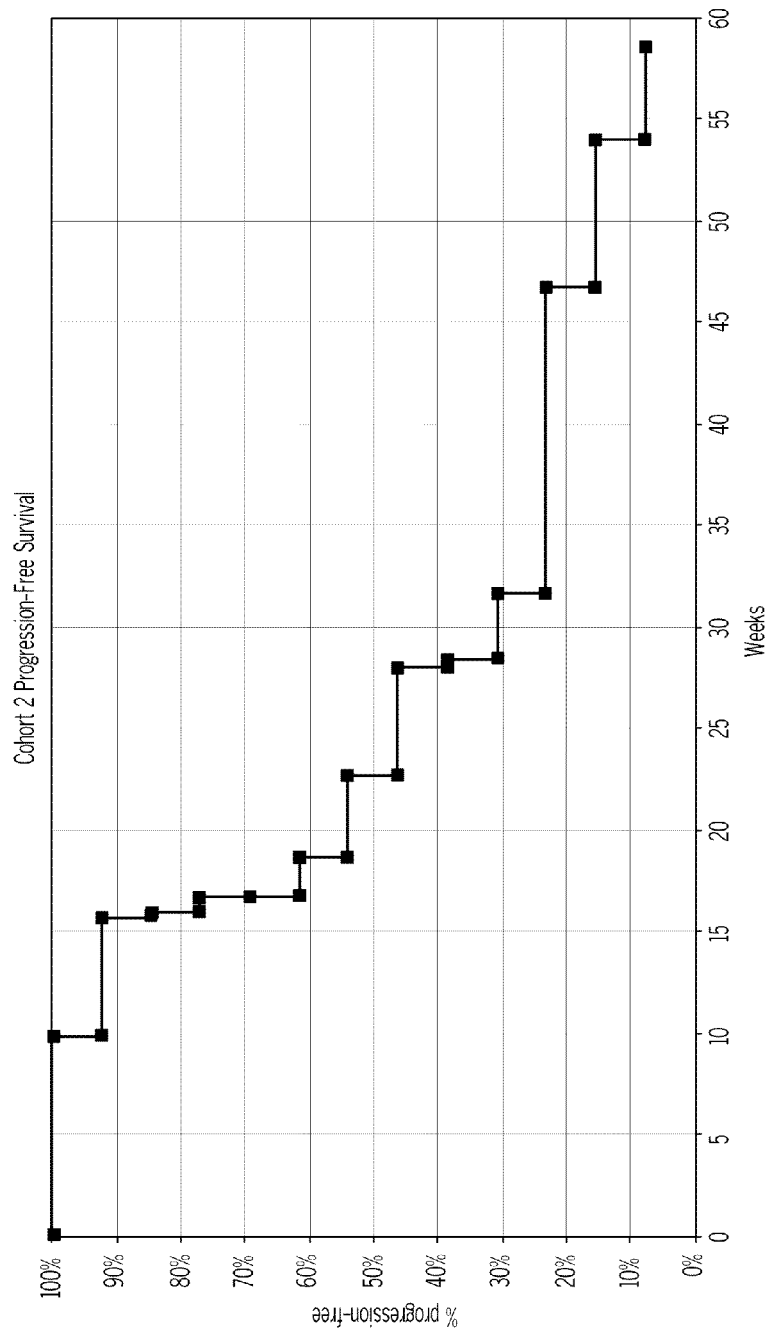
FIG. 14 depicts assessed TTP in patients of cohort group 2 (cohort 2).

Time to disease progression (TTP) is an acceptable clinical end point in HRPC studies. TTP also is a pivotal trial end point in current Phase III clinical trials. Disease progression in patients in both cohort groups were assessed and depicted in FIGS. 13 and 14.

The median TTP in cohort group 1 is 58 weeks (See FIG. 13) and for cohort group 2 it is 23 weeks (See FIG. 14), as determined by the time point at which the percent progression-free patients reaches 50%.

The findings of this study are significant for several reasons, for example,

1. The effects of vaccine therapy on PSADT were not known until this study. The effects were maintained over a prolonged period of time. PSAV data show reduced velocities for periods of 6 to 18 months in about 40% of the patients (See FIGS. 11 and 12). According to recent studies, PSADT and PSAV are predictors of prostate cancer disease progression and survival in HRPC (see Nelson et al., 2004 ASCO Annual Meeting, Abstract No. 4554 and D'Amico et al., 2004 ASCO Annual Meeting, Abstract No. 4506).

2. Median TTP in cohort group 1, using standard criteria, is observed to be 58 weeks (see FIG. 13). Whereas, median TTP generally for patients with no bone metasteses is known in the art to be about 26-28 weeks (see *Atlas of Clinical Urology*, Ed. Peter T. Scardino Md. (1999, 2002); Carducci et al., *J Clin Oncology* (2003) 21:697-689; Small et al., *J Clin Oncology* (2000) 18:3894-3903).

3. Median TTP in patients with asymptomatic bone metasteses is known in the art to be about 9 weeks (see *Proc. Am Asso Cancer Res* (July 2003) vol. 44, 2nd ed., Abstract 5396). In contrast, Median TTP in cohort group 2 is found to be 23 weeks in this study. And 4. The patient population studies in ONY-P1 trial was composed of "all corners", and was not selected or subdivided on the basis of disease severity. For example, patient population was selected or subdivided using the Gleason scores to differentiate between grades of disease by other investigators (see *Proc. Am Asso Cancer Res* (July 2003) vol. 44, 2nd ed., Abstract 5396).

The apparent efficacy of ONY-P1 appeared to be surprising while compared to previous trials using other vaccines; and Eaton et al., *BJU International* (2002) 89:19-26), wherein it was possible to measure effects in patients with bone metastases which are comparable to those observed in patients without bone disease, i.e. at an earlier stage of disease progression. Thus, based on the previous trials, it is not possible to predict clear-cut effects in patients without bone metastases. Therefore, ONY-P1 is significantly more effective in treating prostate cancer, for example, than the combinations of cell lines reported previously (Eaton et al., *BJU International* (2002) 89:19-26).

It is to be understood that while the invention has been described in detail by way of example and illustration for the purpose of clarity of teaching, the foregoing description is not intended to limit the scope of the invention. Other aspects, advantages, and modifications that are apparent to one of skill in the art in light of the teachings of this invention are within the scope of the following claims.

Each document cited herein is incorporated by reference in its entirety. Great Britain patent application No. 9827103.4, filed Dec. 10, 1998, PCT/GB99/04135, filed Dec. 9, 1999 and U.S. patent application Ser. No. 09/857,690, filed Jun. 8, 2001 are incorporated in their entireties by reference.

We claim:

1. A method of increasing PSA doubling times (PSADT) in prostate cancer comprising:
   I) providing an allogeneic immunotherapeutic composition comprising
      a) a non-specific immune stimulant;
      b) cells from an allogeneic cell line derived from a primary non-metastasized prostate cancer biopsy;
      c) cells from an allogeneic cell line derived from a metastasized prostate cancer biopsy; and
      d) cells from an allogeneic normal prostate cell line; and
   II) administering an effective amount of the allogeneic immunotherapeutic composition to a prostate cancer patient, wherein the prostate cancer has metastasized to a tissue selected from the group consisting of bone, lymph node, brain and liver.

2. A method of increasing PSADT in prostate cancer comprising administering an allogeneic immunotherapeutic composition to a prostate cancer patient, wherein the prostate cancer has metastasized to a tissue selected from the group consisting of bone, lymph node, brain and liver, and wherein the allogeneic immunotherapeutic composition comprises:
   a) a non-specific immune stimulant;
   b) cells from an allogeneic cell line derived from a primary non-metastasized prostate cancer biopsy;
   c) cells from an allogeneic cell line derived from a metastasized prostate cancer biopsy; and
   d) cells from an allogeneic normal prostate cell line.

3. A method of increasing PSADT in hormone-resistant prostate cancer comprising administering an allogeneic immunotherapeutic composition to a prostate cancer patient, wherein the hormone-resistant prostate cancer has metastasized to a tissue selected from the group consisting of bone, lymph node, brain and liver, and wherein the allogeneic immunotherapeutic composition comprises:
   a) a non-specific immune stimulant;
   b) cells from an allogeneic cell line derived from a primary non-metastasized prostate cancer biopsy;
   c) cells from an allogeneic cell line derived from a metastasized prostate cancer biopsy; and
   d) cells from an allogeneic normal prostate cell line.

4. The method of claim 2, wherein the non-specific immune stimulant comprises one or more of bacille Calmette-Guerin, a *Mycobacterium, Mycobacterium vaccae*, Tetanus toxoid, Diphtheria toxoid, *Bordetella Pertussis*, interleukin 2, interleukin 12, interleukin 4, interleukin 7, Complete Freund's Adjuvant, and Incomplete Freund's Adjuvant.

5. The method of claim 2, wherein the non-specific immune stimulant comprises inactivated *Mycobacterium vaccae bacilli*.

6. The method of claim 2, wherein the non-specific immune stimulant comprises inactivated bacilli Calmette-Guerin.

7. The method of claim 2, wherein the allogeneic immunotherapeutic composition further comprises cells from at least one other cell line derived from a prostate cancer that has metastasized to one or more tissues selected from the group consisting of the lymph nodes, bone, brain and liver.

8. The method of claim 2, wherein the allogeneic cells are lethally irradiated to ensure that the cells are replication incompetent.

9. The method of claim 2, wherein the allogeneic immunotherapeutic composition further comprises a cryoprotectant.

10. The method of claim 9, wherein the cryoprotectant comprises at least one of 10-30% v/v aqueous glycerol, 5-20% v/v dimethyl sulphoxide and 5-20% w/v human serum albumin.

11. The method of claim 2, wherein the cells of b) are P4E6 cells.

12. The method of claim 4, wherein the cells of c) are derived from LnCAP cell line.

13. The method of claim 4, wherein the cells of d) are derived from OnyCap-23 or PNT-2 cells.

* * * * *